(12) United States Patent
Visvader et al.

(10) Patent No.: US 7,700,271 B2
(45) Date of Patent: Apr. 20, 2010

(54) METHOD OF DIAGNOSIS AND TREATMENT AND AGENTS USEFUL FOR SAME

(75) Inventors: Jane Ellen Visvader, Kew (AU); Geoffrey John Lindeman, Kew (AU); Eleanor Y. M. Sum, Preston (AU); Lorraine Ann O'Reilly, Cheltenham (AU)

(73) Assignee: The Walter and Eliza Hall Institute of Medical Research, Victoria (AU)

( * ) Notice: Subject to any disclaimer, the term of this patent is extended or adjusted under 35 U.S.C. 154(b) by 0 days.

(21) Appl. No.: 10/799,797

(22) Filed: Mar. 12, 2004

(65) Prior Publication Data

US 2005/0048528 A1    Mar. 3, 2005

Related U.S. Application Data

(63) Continuation of application No. PCT/AU02/01246, filed on Sep. 12, 2002.

(30) Foreign Application Priority Data

Sep. 12, 2001 (AU) .................................. PR7618

(51) Int. Cl.
 C12Q 1/00 (2006.01)
 G01N 33/53 (2006.01)
 G01N 33/573 (2006.01)

(52) U.S. Cl. ........................ 435/4; 435/7.1; 435/7.23

(58) Field of Classification Search .............. 435/7.1, 435/7.21; 436/512
 See application file for complete search history.

(56) References Cited

U.S. PATENT DOCUMENTS

2003/0092009 A1* 5/2003 Palm .............................. 435/6
2006/0148008 A1   7/2006 Hart et al.

FOREIGN PATENT DOCUMENTS

| WO | WO 00/29852    | 5/2000 |
| WO | WO 01/38878 A2 | 5/2001 |
| WO | WO 02/40716 A2 | 5/2002 |
| WO | WO 2004/073739 A1 | 9/2004 |

OTHER PUBLICATIONS

W. Paul, Fundamental Immunology, 3rd Edition, 1993.*
Rudikoff et al., Proc. Natl. Acad. Sci. USA 1982 vol. 79: p. 1979.*
Visvader et al., PNAS, vol. 98, p. 14452-14457, Dec. 2001.*
Burgess et al, Journal of Cell biology, vol. 111, p. 2129-2138, 1990.*
Kenny et al., PNAS, vol. 95, p. 11257-11262, 1998 (IDS, Feb. 4, 2005).*
Grutz et al., Oncogene vol. 17, p. 2799-2803, 1998 (IDS, Feb. 4, 2005).*
Tse et al, Mammalian genome vol. 10, p. 1089-94, 1999.*
Yu et al, molecular Cancer, vol. 7, p. 93, Dec. 2008.*
Visvader et al PNAS, vol. 98, p. 14452-14457, Dec. 2001, (IDS filed Feb. 4, 2005, p. 6, item 1).*
Visvader, Jane E., et al., "The LIM domain gene *LMO4* inhibits differentiation mammary epithelial cells in vitro and is overexpressed in breast cancer", Proceedings of the National Academy of Sciences (2001), vol. 98, No. 25, pp. 14452-14457.
Kenny, Daryn A., et al., "Identification and characterization of *LM04*, an LMO gene with a novel pattern of expression during embryogenesis", Proceedings of the National Academy of Sciences (1998), vol. 95, pp. 11257-11262.
Sugihara, Tod M., et al., "Mouse Deformed epidermal autoregulatory factor 1 recruits a LIM domain factor, LMO-4, and CLIM coregulators", Proceedings of the National Academy of Sciences (1998), vol. 95, pp. 15418-15423.
Grutz, G., et al., "Identification of the *LMO4* gene encoding an interaction partner of the LIM-binding protein LDB1/NL11: a candidate for displacement by LMO proteins in T cell acute leukemia", Oncogene (1998), vol. 17, pp. 2799-2803.
Tse, Eric, et al., "Characterization of the *Lmo4* gene encoding a LIM-only protein: genomic organization and comparative chromosomal mapping", Mammalian Genome (1999), vol. 10, pp. 1089-1094.
Racevskis, J. et al., "Molecular cloning of *LM04*, a new human LIM domain gene", *Biochimica et Biophysica Acta 1445*: 148-153 (1999).
Communication stating Notice of Reasons for Rejection dated Sep. 10, 2008 Re: Japanese Patent Application No, 2003-527424.
Communication Pursuant to Article 94(3) EPC dated Oct. 13, 2008 from the European Patent Office Re: European Patent Application No. 02753953.5.
Visvader et al,, "The LIM-domain binding protein Ldb1 and its partner LM02 act as negative regulators of erythroid differentiation", *Proc. Nad. Acad. Sci. USA 94*: 13707-13712 (1997).

* cited by examiner

*Primary Examiner*—Larry R. Helms
*Assistant Examiner*—Lei Yao
(74) *Attorney, Agent, or Firm*—Scully, Scott, Murphy & Presser, P.C.

(57) ABSTRACT

The present invention relates generally to a method for detecting an aberrant cell, and more particularly an aberrant epithelial cell, in a subject or in a biological sample from said subject and agents useful for same. More particularly, the present invention relates to a method of deleting an aberrant mammary epithelial cell. The presence of the aberrant cell or group of aberrant cells provides an indication of a particular disease or condition or a propensity for development of a disease or condition.

6 Claims, 12 Drawing Sheets

Figure 7
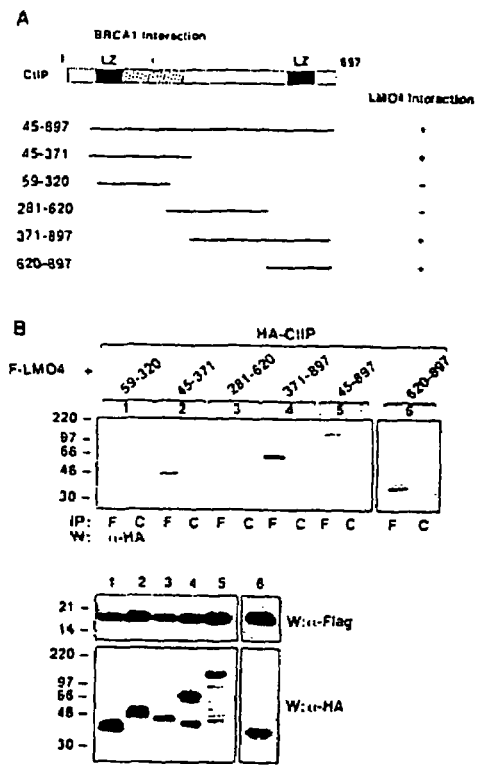
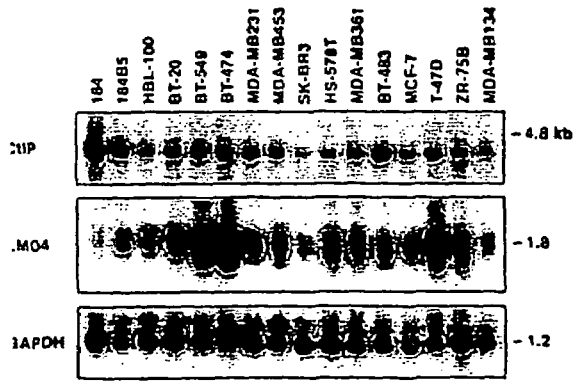
Figure 8

Figure 9
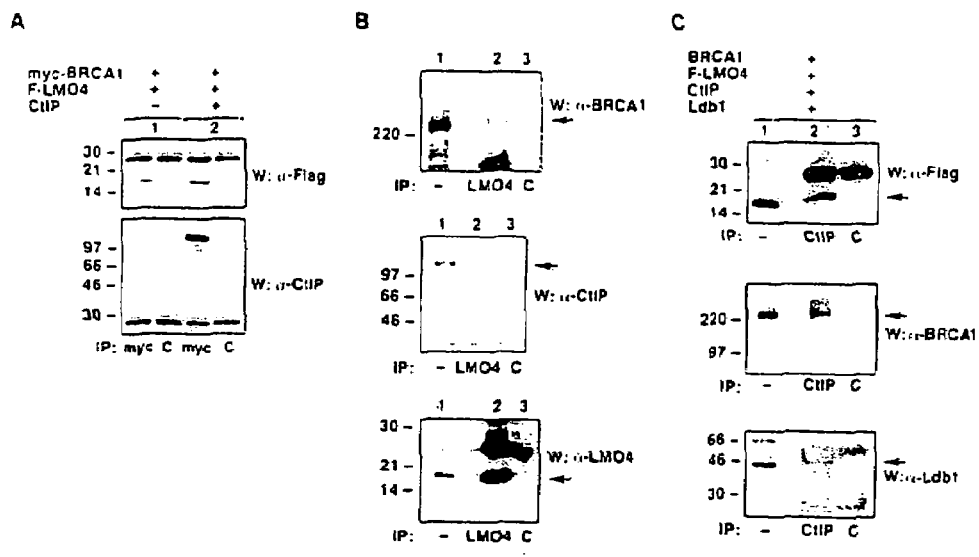
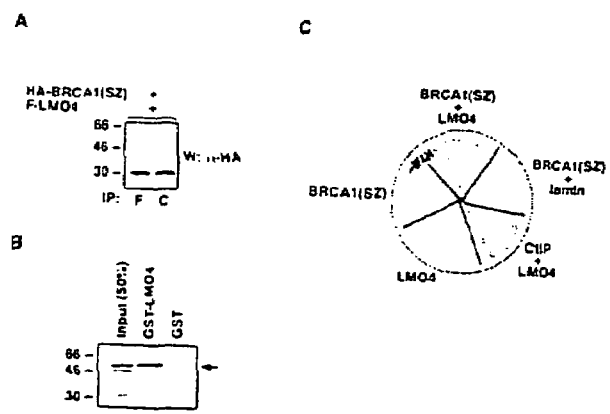
Figure 10

SEQUENCE LISTING

```
<160> NUMBER OF SEQ ID NOS: 10

<210> SEQ ID NO 1
<211> LENGTH: 25
<212> TYPE: DNA
<213> ORGANISM: Artificial sequence
<220> FEATURE:
<223> OTHER INFORMATION: synthetic beta-casein forward primer

<400> SEQUENCE: 1
atgaaggtct tcatcctcgc ctgcc                                          25

<210> SEQ ID NO 2
<211> LENGTH: 26
<212> TYPE: DNA
<213> ORGANISM: Artificial sequence
<220> FEATURE:
<223> OTHER INFORMATION: synthetic beta-casein reverse primer

<400> SEQUENCE: 2
gctggaccag agactgagga aggtgc                                         26

<210> SEQ ID NO 3
<211> LENGTH: 24
<212> TYPE: DNA
<213> ORGANISM: Artificial sequence
<220> FEATURE:
<223> OTHER INFORMATION: synthetic Wap forward primer

<400> SEQUENCE: 3
tagcagcaga ttgaaagcat tatg                                           24
```

<210> SEQ ID NO 4
<211> LENGTH: 20
<212> TYPE: DNA
<213> ORGANISM: Artificial sequence
<220> FEATURE:
<223> OTHER INFORMATION: synthetic Wap reverse primer

<400> SEQUENCE: 4
gacaccggta ccatgcgttg                                                      20

<210> SEQ ID NO 5
<211> LENGTH: 35
<212> TYPE: DNA
<213> ORGANISM: Artificial sequence
<220> FEATURE:
<223> OTHER INFORMATION: synthetic forward primer for generating LMO4

<400> SEQUENCE: 5
cgcggatccc cggctccctc tcctggaagc gctgc                                     35

<210> SEQ ID NO 6
<211> LENGTH: 33
<212> TYPE: DNA
<213> ORGANISM: Artificial sequence
<220> FEATURE:
<223> OTHER INFORMATION: synthetic reverse primer for generating LMO4

<400> SEQUENCE: 6
cgcggatcct cagcagacct tctggtctgc cag                                       33

<210> SEQ ID NO 7
<211> LENGTH: 30
<212> TYPE: DNA
<213> ORGANISM: Artificial sequence
<220> FEATURE:
<223> OTHER INFORMATION: synthetic forward primer for amplifying the
      first LIM domain of LMO4

<400> SEQUENCE: 7
cgcggatcct gaatccgggc agcagctcgc                                           30

<210> SEQ ID NO 8
<211> LENGTH: 36
<212> TYPE: DNA
<213> ORGANISM: Artificial sequence
<220> FEATURE:
<223> OTHER INFORMATION: synthetic reverse primer for amplifying the
      first LIM domain of LMO4

<400> SEQUENCE: 8
cgcggatcct cacccaaata acctaatgta gtcatt                                    36

<210> SEQ ID NO 9
<211> LENGTH: 34
<212> TYPE: DNA
<213> ORGANISM: Artificial sequence
<220> FEATURE:
<223> OTHER INFORMATION: synthetic forward primer for amplifying the
      second LIM domain of LMO4

<400> SEQUENCE: 9
cgcggatccg gttatttggg aatagcggtg cttg                                      34

<210> SEQ ID NO 10
<211> LENGTH: 33
<212> TYPE: DNA

```
<213> ORGANISM: Artificial sequence
<220> FEATURE:
<223> OTHER INFORMATION: synthetic reverse primer for amplifying the
      second LIM domain of LMO4

<400> SEQUENCE: 10
cgcggatcct cagcagacct tctggtctgc cag                                      33
```

US 7,700,271 B2

METHOD OF DIAGNOSIS AND TREATMENT AND AGENTS USEFUL FOR SAME

CROSS REFERENCE TO RELATED APPLICATIONS

The present application is a continuation of International Application No. PCT/AU02/01246, filed on Sep. 12, 2002.

FIELD OF THE INVENTION

The present invention relates generally to a method for detecting an aberrant cell, and more particularly an aberrant epithelial cell, in a subject or in a biological sample from said subject and agents useful for same. More particularly, the present invention relates to a method of deleting an aberrant mammary epithelial cell. The presence of the aberrant cell or group of aberrant cells provides an indication of a particular disease or condition or a propensity for development of a disease or condition. More particularly, the present invention contemplates a method for detecting a cell associated with breast cancer or having a propensity to develop into a breast cancer in a subject or in a biological sample from said subject by determining the relative increase in the presence of the LM04 protein or a related protein or a relative increase in LM04 activity or a relative increase in the presence of expression products from a gene encoding the LM04 protein or a related protein. The present invention further provides a method for diagnosing the presence of a cancer or cancerous-like growth, in particular breast cancer in a subject or in a biological sample from said subject by screening for up-regulation of LM04 or a related protein in a cell or group of cells or an up-regulation in the presence of expression products of genetic sequences encoding LM04 or a related protein. The present invention provides diagnostic agents useful for detecting LM04 or expression products of genetic material encoding LM04. Such diagnostic agents include immunointeractive molecules, such as antibodies, and genetic probes for detecting expression products of LM04 genes. The present invention further provides genetically modified animals exhibiting altered levels of LM04 Such animals are useful models for screening for anti-cancer agents.

The present invention still further relates generally to a method of modulating LM04 related cellular proliferation and to agents useful for same. More particularly, the present invention contemplates a method of modulating breast cell proliferation by modulating LM04 nucleic acid expression and/or LM04 functioning. The method of the present invention is useful, inter alia, in the treatment and/or prophylaxis of conditions characterised by aberrant, unwanted or otherwise inappropriate LM04 regulated cellular proliferation. The present invention is further directed to methods for identifying and/or designing agents capable of modulating LM04 regulated cellular proliferation.

BACKGROUND OF THE INVENTION

Bibliographic details of the publications referred to by both author and numerically in this specification are collected at the end of the description.

The reference to any prior art in this specification is not, and should not be taken as, an acknowledgment or any form of suggestion that that prior art forms part of the common general knowledge in Australia.

The LIM domain defines a conserved cysteine-rich structure comprising two tandemly repeated zinc fingers and is found in a large group of diverse proteins (reviewed in 1, 2). This motif, originally identified in LIM-homeodomain transcription factors, may either occur alone (as one or more copies) or in association with heterologous domains such as a protein kinase or homeobox domain. Targeted gene disruption has established that. LIM domain-containing proteins have critical functions in cell-fate specification and differentiation (3).

The LMO family consists of four members (designated LM01-4), each of which comprises two tandem LIM domains. LM02 is essential for embryonic hematopoiesis and is thought to function at the level of the pluripotent stem cell (11). Little is known about the function of LM03, discovered on the basis of sequence homology. The most recently described member, LM04, was isolated by virtue of its interaction with Ldb1/NL1/CLIM and in an expression screen with autologous serum (12-15). Ldb1 is a multifunctional adaptor protein that interacts with LMO proteins and other nuclear LIM-containing factors (16-19). The LM04 gene is widely expressed in both embryonic and adult tissues (12, 13, 15). Like the other members of this family, it is presumed that LM04 is a transcriptional cofactor that primarily functions as a docking site for other factors. LM04 may also contribute an activation or repression domain to influence transcriptional activity.

In work leading up to the present invention the inventors have determined that LM04 plays a role in mammary development and in breast oncogenesis. The LM04 gene is developmentally regulated in mammary epithelium and LM04 together with Ldb1 have been found to act as negative regulators of mammary epithelial differentiation. Significantly, overexpression of the LM04 gene was found in greater than 50% of primary breast cancers, indicating that this protein contributes to the pathogenesis of breast cancer.

SUMMARY OF THE INVENTION

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The subject specification contains nucleotide sequence information prepared using the programme PatentIn Version 3.0, presented herein after the bibliography. Each nucleotide sequence is identified in the sequence listing by the numeric indicator <201> followed by the sequence identifier (eg. <210>1, <210>2, etc). The length, type of sequence (DNA, etc) and source organism for each nucleotide sequence is indicated by information provided in the numeric indicator fields <211>, <212> and <213>, respectively. Nucleotide sequences referred to in the specification are identified by the indicator SEQ ID NO: followed by the sequence identifier (eg. SEQ ID NO:1, SEQ ID NO:2, etc.). The sequence identifier referred to in the specification correlates to the information provided in numeric indicator field <400> in the sequence listing, which is followed by the sequence identifier (eg. <400>1, <400>2, etc). That is SEQ ID NO:1 as detailed in the specification correlates to the sequence indicated as <400>1 in the sequence listing.

One aspect of the present invention contemplates a method for detecting an aberrant cell in a subject or in a biological sample from said subject, said method comprising contacting cells or cell extracts from said subject or said biological sample with an immunointeractive molecule specific for LM04 or antigenic portion thereof and screening for the level of immunointeractive molecule-LM04 complex formation wherein an elevated presence of said complex relative to a normal cell is indicative of an aberrant cell.

Another aspect of the present invention contemplates a method for detecting an aberrant epithelial cell in a subject or in a biological sample from said subject, said method comprising contacting mammary cells or mammary cell extracts from said subject or said biological sample with an immunointeractive molecule specific for LM04 or antigenic portion thereof and screening for the level of immunointeractive molecule-LM04 complex formation wherein an elevated presence of said complex relative to a normal epithelial cell is indicative of an aberrant epithelial cell.

Yet another aspect of the present invention contemplates a method for detecting an aberrant mammary cell in a subject or in a biological sample from said subject, said method comprising contacting mammary cells or mammary cell extracts from said subject or said biological sample with an immunointeractive molecule specific for LM04 or antigenic portion thereof and screening for the level of immunointeractive molecule-LM04 complex formation wherein an elevated presence of said complex relative to a normal mammary cell is indicative of an aberrant mammary cell.

In a related aspect, the present invention provides a method for detecting an aberrant cell in a subject or in a biological sample from said subject, said method comprising screening the level of a transcription product of a gene encoding LM04 wherein an elevated level of said expression product compared to a normal cell is indicative of an aberrant cell.

In another aspect, there is provided a method for detecting an aberrant epithelial cell in a subject or in a biological sample from said subject, said method comprising screening the level of a transcription product of a gene encoding LM04 wherein an elevated level of said expression product compared to a normal epithelial cell is indicative of an aberrant epithelial cell.

In yet another aspect there is provided a method for detecting an aberrant mammary cell in a subject or in a biological sample from said subject, said method comprising screening the level of a transcription product of a gene encoding LM04 wherein an elevated level of said expression product compared to a normal mammary cell is indicative of an aberrant mammary cell.

Still yet another aspect of the present invention contemplates a method for diagnosing the presence of a neoplasm or neoplasm-like growth in a subject, said method comprising contacting cells or cell extracts from said subject or a biological sample from said subject with a LM04-binding effective amount of an antibody having specificity for said LM04 or an antigenic determinant or epitope thereon and then quantitatively or qualitatively determining the level of a LM04-antibody complex wherein the presence of elevated levels of said complex compared to a normal cell is indicative of the presence of a neoplasm.

Yet still another aspect of the present invention provides a method for diagnosing the presence of a neoplasm in a subject, said method comprising obtaining mRNA from cells of said subject or from a biological sample from said subject and optionally generating cDNA and contacting said mRNA or cDNA with a genetic probe capable of hybridizing to and/or amplifying all or part of a nucleotide sequence encoding LM04 or its complementary nucleotide sequence and then detecting the level of said mRNA or cDNA wherein the presence of elevated levels of said mRNA or cDNA compared to normal controls is indicative of the presence of a neoplasm.

A further aspect of the present invention provides an antibody and in particular a monoclonal antibody for use in immunological assays for LM04 or for cancer imaging in vivo. The antibody may be directed either to the LM04 protein or the LM04 mRNA, for example In another aspect the subject antibody is 16H2 or 20F8 or derivative, homologue, analogue, chemical equivalent, mutant or mimetic thereof.

Yet another further aspect of the present invention contemplates a deimmunized antibody molecule having specificity for an epitope recognized by a monoclonal antibody to LM04 wherein at least one of the CDRs of the variable domain of said deimmunized antibody is derived from the said monoclonal antibody to LM04 and the remaining immunoglobulin-derived parts of the deimmunized antibody molecule are derived from an immunoglobulin or an analogue thereof from the host for which the antibody is to be deimmunized.

Still another aspect of the present invention contemplates an assay to detect LM04 including the steps of:—
  (1) contacting a monoclonal antibody specific to LM04 or an antigenic determinant thereon with a biological sample suspected of containing a cell containing said LM04; and
  (2) subjecting the complex formed in step (1) to a signal detection step.

Another aspect of the present invention contemplates a method for detecting neoplastic cells in a human patient, said method comprising introducing into said patient a deimmunized form of a non-human derived monoclonal antibody specific for human LM04 or an antigenic determinant thereon labelled with a reporter molecule, allowing dissemination of the labelled antibody throughout the circulatory system, or to selected parts of the circulatory system and then subjecting said patient to reporter molecule-detection means to identify the location of the antibody.

Yet another aspect of the present invention provides a method of detecting, in a sample, LM04 or fragment, variant or derivative thereof comprising contacting the sample with an antibody or fragment or derivative thereof and detecting the level of a complex comprising said antibody and LM04 or fragment, variant or derivative thereof compared to normal controls wherein elevated levels of LM04 is indicative of cancer growth.

Still another aspect of the present invention provides a method of monitoring for the onset or progression of a neoplasm in a subject, said method comprising screening for the level of LM04 or a transcription product of a gene encoding LM04 in a biological sample from said subject wherein an elevated level of said LM04 or transcription product compared to the levels of a normal cell is indicative of a neoplasm.

Yet still another aspect of the present invention contemplates the use of a monoclonal antibody to LM04 in the manufacture of a quantitative or semi-quantitative diagnostic kit to determine relative levels of LM04 in suspected neoplastic cells from a patient.

Still yet another aspect of the present invention provides a method of modulating LM04 regulated cellular proliferation, said method comprising contacting said cell with an effective amount of an agent for a time and under conditions sufficient to modulate LM04 expression or LM04 functional activity wherein inhibiting or otherwise antagonising said expression or activity down-regulates said cellular proliferation.

The present invention more particularly provides a method of modulating LM04-regulated mammary cell proliferation, said method comprising contacting said cell with an effective amount of an agent for a time and under conditions sufficient to modulate LM04 expression or LM04 functional activity wherein inhibiting or otherwise antagonising said expression or activity down-regulates said cellular proliferation.

Another further aspect of the present invention provides a method for detecting an agent capable of modulating LM04 expression or LM04 functional activity said method comprising contacting a cell or extract thereof containing said LM04 or LM04 with a putative agent and detecting an altered expression phenotype associated with said interaction.

Another further aspect of the present invention is directed to the method for the treatment and/or prophylaxis of a conditions characterised by aberrant, unwanted or otherwise inappropriate LM04-regulated proliferative activity in a mammal, said method comprising administering to said mammal an effective amount of an agent for a time and under conditions sufficient to modulate LM04 expression or LM04 functional activity wherein inhibiting or otherwise antagonising said expression or activity down-regulates said cellular proliferation.

In yet another further aspect there is provided a method for the treatment and/or prophylaxis of a neoplastic condition said method comprising administering to said mammal an effective amount of an agent for a time and under conditions sufficient to down-regulate LM04 expression or LM04 functional activity wherein inhibiting or otherwise antagonising said expression or activity down-regulates cellular proliferation.

Still another further aspect of the present invention contemplates the use of an agent, as hereinbefore defined, in the manufacture of medicament for the treatment of a condition in a mammal, which condition is characterised by aberrant, unwanted or otherwise inappropriate LM04-regulated cellular proliferation, wherein said agent modulates LM04 expression or LM04 activity and wherein inhibiting or otherwise antagonising said expression or activity down-regulates said cellular proliferation.

In yet another further aspect, the present invention contemplates a pharmaceutical composition comprising the modulatory agent as hereinbefore defined together with one or more pharmaceutically acceptable carriers and/or diluents. Said agents are referred to as the active ingredients.

Yet another aspect of the present invention relates to the agent as hereinbefore defined, when used in the method of the present invention.

BRIEF DESCRIPTION OF THE DRAWINGS

FIG. 7: Two regions within CtIP specifically interact with LMO4. A, Schematic representation of wild-type CtIP and deletion mutant constructs that were tested for interaction with LMO4 in mammalian cells. The region that associates with BRCA1 and two putative leucine zipper (LZ) domains are indicated. A summary of each mutant's ability to interact with LMO4 is shown. B, 293T cells were transfected with expression constructs encoding HA-tagged derivatives of CtIP (lanes 1-6), together with that encoding Flag-tagged LMO4. Lysates were prepared and proteins immunoprecipitated using anti-Flag monoclonal antibody (F) or control isotype-matched (C) monoclonal antibody. After SDS-PAGE electrophoresis, western blotting was performed using α-HA antibody, specific for CtIP protein. Western blot analysis confirmed expression of Flag-LMO4 and CtIP mutant proteins (lower panels).

FIG. 8: Coexpression of LMO4 and CtIP in breast epithelial cells. Northern blot analysis of poly(A)$^+$ RNA (3 μg) isolated from the indicated 'normal'(184) and human breast cancer cell lines. The filter was sequentially hybridized with human CtIP and LMO4 cDNA probes, followed by the control GAPDH probe.

FIG. 9: LMO4 forms a complex with CtIP and BRCA1 in vivo and directly interacts with BRCA1. A, Specific interaction between LMO4, CtIP and BRCA1 in vivo. 293T cells were transfected with expression constructs encoding Flag-tagged LMO4 and myc-tagged BRCA1 in the presence (lane 2) or absence of plasmid encoding CtIP (lane 1). Lysates were prepared and proteins were immunoprecipitated with anti-myc or control (C) monoclonal antibody, then fractionated by electrophoresis, before blotting with either anti-Flag or anti-CtIP antibody. Expression of individual proteins in these cell extracts was confirmed by western blotting (data not shown). B, Endogenous LMO4, BRCA1 and CtIP proteins associate in HBL100 epithelial cells. Nuclear lysates were immunoprecipitated with a rat anti-LMO4 monoclonal (lane 2) or control antibody (lane 3), then immunoblotted with anti-BRCA1 (upper panel) or anti-CtIP (middle panel) monoclonal antibody. The immunoprecipitate was divided between two SDS-polyacrylamide gels, one of which underwent extended electrophoresis for detection of BRCA1 (220 kD) while the other was immunoblotted with anti-CtIP antibody. As a control, immunoprecipitate was also blotted with anti-LMO4 monoclonal antibody (lower panel). Lysate from HBL100 cells was loaded in an adjacent lane to provide a size control for the respective proteins (lane 1), indicated by arrows. C, Interaction between LMO4, CtIP, BRCA1 and Ldb1 in mammalian cells. Extracts derived from 293T cells transfected with expression vectors encoding BRCA1, Flag-tagged LMO4, CtIP and Ldb1 were immunoprecipitated with anti-CtIP antibody (lane 2) or control antibody (lane 3), then immunoblotted with the indicated antibodies. Western blot analysis confirmed high level expression of individual proteins in these transfectants (lane 1).

FIG. 10: The C-terminal BRCT domains of BRCA1 mediate interaction with LMO4. A, 293T cells were transfected with expression constructs encoding Flag-tagged LMO4 and the C-terminal region (SZ) of BRCA1 carrying an HA-tag. Lysates were immunoprecipitated with anti-Flag (F) or control (C) antibody, then western blotted with anti-HA antibody. B, LMO4 and the BRCT domain interact in vitro. In vitro translated $^{35}$S-methionine-labeled BRCA1 (aa 1528-1863), corresponding to the SZ fragment, was incubated with GST-LMO4 fusion protein immobilised on glutathione sepharose. Bound proteins were analysed by SDS-PAGE. Arrow depicts the BRCA1-SZ protein. C, LMO4 and the BRCT (SZ) region of BRCA1 interact in yeast Hf7c cells. Yeast cells were cotransformed with the indicated expression vectors and plated on media deficient in his, leu and trp. Staining for β-galactosidase activity verified that the His$^+$ colonies obtained for LMO4+CtIP and LMO4+BRCA1 (SZ) transformants were also β-Gal$^+$. No colonies were obtained for Hf7c cells transformed with BRCA1 (SZ)+lamin, BRCA1 (SZ) alone or LMO4 alone.

DETAILED DESCRIPTION OF THE INVENTION

Figure 1:
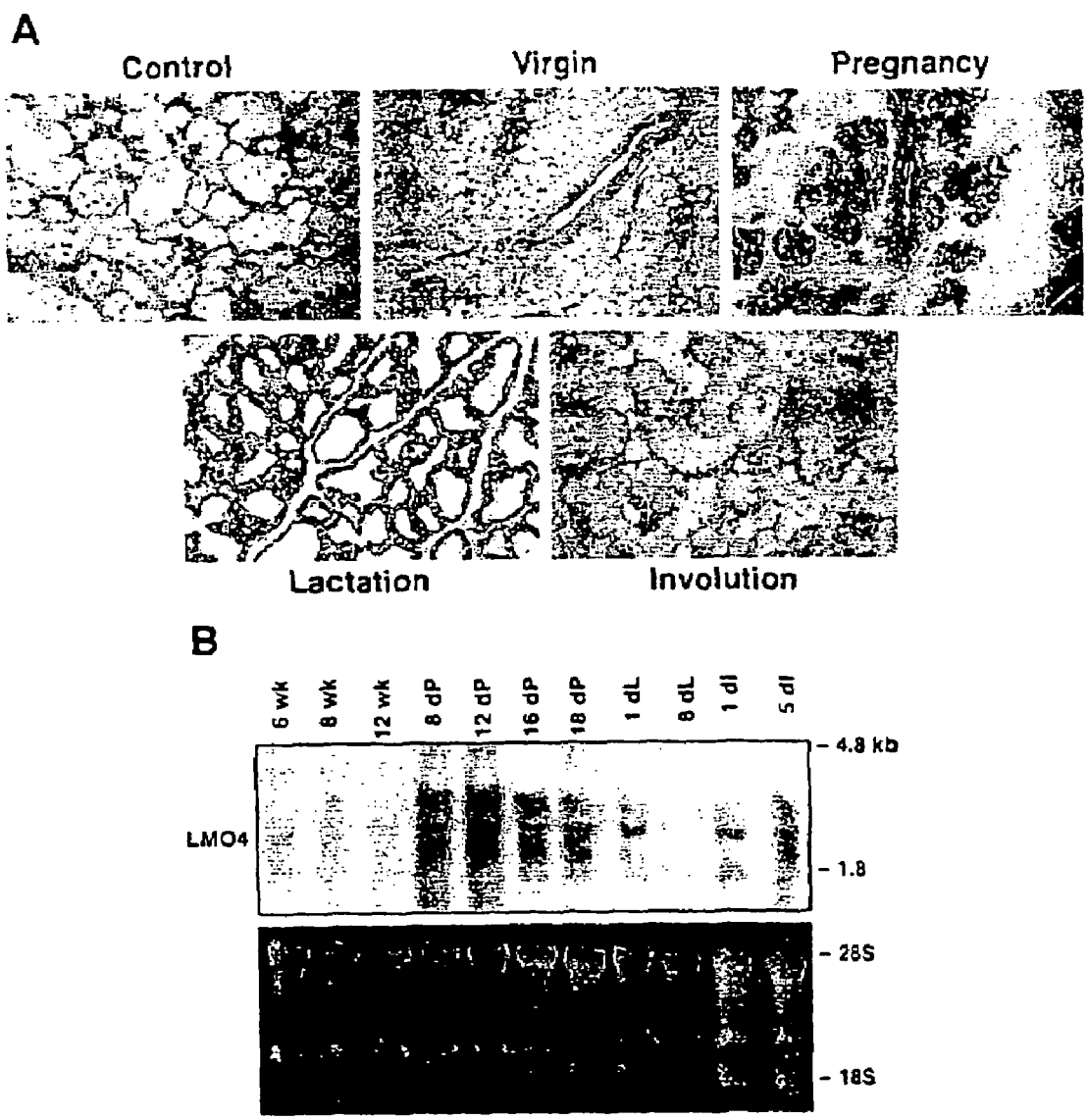
FIG. 1: Lmo4 is abundantly expressed in the lobuloalveolar units during pregnancy. (A) A single layer of ductal epithelium expressing Lmo4 transcripts is evident in the adult mammary gland. RNA expression was assessed by in situ hybridisation using sense (control) and antisense digoxigenin-labeled riboprobes corresponding to full-length mouse Lmo4 sequence. Young adult virgin, 12 day pregnant, 2 day lactating and 4 day involuting mammary glands were analysed. The sense probe was hybridised to sections of 3 day involuting (shown), as well as those of lactating and pregnant mammary glands. Orig. mag. 50× (B) Northern analysis of mammary glands from virgin, pregnant, lactating and force-weaned (involution) mice. Filters containing 20 μg total RNA were hybridised with a mouse Lmo4 probe. The lower molecular weight bands may represent either an alternatively spliced variant of Lmo4 RNA or a cross-hybridising species. The ethidium bromide stained gel showing 28S and 18S ribosomal RNA provides a loading control.

The present invention is predicated in part on the determination that LM04 expression is up-regulated in cancer cells, in particular in epithelial cancer cells, and most particularly in breast cancer cells relative to normal breast cells. The identification of this cancer-specific marker permits development of a range of diagnostic agents, including cancer imaging agents and cancer targeting agents having therapeutic applications. These determinations also permit the rational design of therapeutic and/or prophylactic methods for treating conditions, such as those characterised by aberrant or unwanted LM04 regulated proliferation.

Accordingly, one aspect of the present invention contemplates a method for detecting an aberrant cell in a subject or in a biological sample from said subject, said method comprising contacting cells or cell extracts from said subject or said biological sample with an immunointeractive molecule specific for LM04 or antigenic portion thereof and screening for the level of immunointeractive molecule-LM04 complex formation wherein an elevated presence of said complex relative to a normal cell is indicative of an aberrant cell.

Reference to an "aberrant" cell should be understood as a reference to a cell which exhibits undesirable, unwanted or otherwise inappropriate functional activity. The subject functional activity is preferably inappropriate proliferation or differentiation. Most preferably, the inappropriate functional activity is inappropriate growth such as is exhibited by, for example, a neoplastic cell.

Reference to a "neoplasm" should be understood as a reference to a lesion, tumour or other encapsulated or unencapsulated mass or other form of growth which comprises neoplastic cells. A "neoplastic cell" should be understood as a reference to a cell exhibiting abnormal growth. The term "growth" should be understood in its broadest sense and includes reference to proliferation. In this regard, an example of abnormal cell growth is the uncontrolled proliferation of a cell. The neoplastic cell may be a benign cell or a malignant cell. The subject neoplastic cell may be any cell type such as an epithelial or a non-epithelial cell.

The common medical meaning of the term "neoplasia" refers to "new cell growth" that results as a loss of responsiveness to normal growth controls, e.g. to neoplastic cell growth. A "hyperplasia" refers to cells undergoing an abnormally high rate of growth. However, as used herein, the terms "neoplasia" and "hyperplasia" can be used interchangeably, referring generally to cells experiencing abnormal cell growth rates. Neoplasis and hyperplasis include "tumors" which may be either benign, pre-malignant or malignant.

As used herein, the terms "hyperproliferative" and "neoplastic" are used interchangeably and refer to those cells in an abnormal state or condition characterized by rapid proliferation or neplasm. The terms are meant to include all types of cancerous growths or oncogenic processes, metastatic tissues or malignantly transformed cells, tissues or organs irrespective of histopathologic type or state of invasiveness. "Pathologic hyperproliferative" cells occur in disease states characterized by malignant tumor growth.

The term "carcinoma" is recognized by those skilled in the art and refers to malignancies of epithelial or endocrine tissues including respiratory system carcinomas, gastrointestinal system carcinomas, genitourinary system carcinomas, testicular carcinomas, breast carcinomas, prostatis carcinomas, endocrine system carcinomas and melanomas. Exemplary carcinomas include those forming from tissue of the breast. The term also includes carcinosarcomas, e.g. which include malignant tumors composed of carcinomatous and sarcomatous tissues. An "adenocarcinoma" refers to a carcinoma derived from glandular tissue or in which the tumor cells form recognizable glandular structures.

As detailed hereinbefore the term "neoplasm" as used herein encompasses all the terms discussed in the preceding three paragraphs.

Examples of neoplasms and neoplastic cells encompassed by the present invention include, but are not limited to, central nervous system tumors, Retinoblastoma, head and neck cancers (eg. squamous cell cancers), lung cancer (both small and non-small cell lung cancer), kidney cancers (eg. renal cell adenocarcinoma), pancreatic neoplasias (eg. adenocarcinomas and islet cell tumors), colorectal cancer, cervical cancer, testicular cancer (eg. germ cell tumors), ovarian cancer (eg. ovarian epithelial cancer and ovarian germ cell tumors), lymphomas, leukemias, malignant melanomas, neuroendocrine tumors and carcinoid tumors In one preferred embodiment, the subject aberrant cell is an epithelial cell.

Reference to "epithelial cell" should be understood as a reference to the cell type which can form epithelium and which is derived from either of the endoderm or the ectoderm. Epithelium consists of closely packed cells which form a sheet and generally comprise very little intercellular material. Epithelial cell types can vary thereby giving rise to various types of epithelia including squamous, cuboidal, columnar and ciliated epithelia. There are three main types of epithelial tissue, these being covering/lining epithelium (which generally forms a membrane over the outer surface of the body and walls of the internal cavities, such as the gastrointestinal tract and the respiratory tract), glandular epithelium and sensory epithelium, being the epithelium which can form part of the sensory organs. The phrase "epithelial cells" should also be understood as a reference to cells which exhibit one or more of the morphology, phenotype and/or functional activity of epithelial cells and is also a reference to mutants or variants thereof. "Variants" include, but are not limited to, cells exhibiting some but not all of the morphological or phenotypic features or functional activities of epithelial cells at any differentiative stage of development. "Mutants" include, but are not limited to, epithelial cells which have been naturally or non-naturally modified such as cells which are genetically modified.

It should also be understood that the cells of the present invention may be at any differentiative stage of development. Accordingly, the cells may be immature and therefore functionally incompetent in the absence of further differentiation. In this regard, highly immature cells such as stem cells, which retain the capacity to differentiate into a particular cell type, such as an epithelial cell or a mammary cell, should nevertheless be understood to satisfy the definition of "epithelial cell" or "mammary cell" as utilised herein due to their capacity to differentiate into these cell types under appropriate conditions.

Accordingly, in one preferred embodiment the present invention contemplates a method for detecting an aberrant epithelial cell in a subject or in a biological sample from said subject, said method comprising contacting mammary cells or mammary cell extracts from said subject or said biological sample with an immunointeractive molecule specific for LM04 or antigenic portion thereof and screening for the level of immunointeractive molecule-LM04 complex formation wherein an elevated presence of said complex relative to a normal epithelial cell is indicative of an aberrant epithelial cell.

In another preferred embodiment, the subject aberrant cell is a mammary cell.

Without limiting the present invention to any one theory or mode of action, the mammary gland is a structurally dynamic organ which varies with age, menstrual cycle and reproductive status. It is a branched tubuloalveolar gland exhibiting secretory acinii which are grouped with inner lobules and drain into intralobular ducts which in turn drain into interlobular ducts. The lobules are organised into 15-20 lobes, each of which empty into separate lactiferous sinuses and from there into lactiferous ducts. The intralobular stroma consists of a loose connective tissue with a zone of hormone sensitive fibroblasts surrounding the lobular epithelial components. These are thought to take part in epithelial/basement membrane/stromal inductive interactions during morphogenesis and differentiation. The mammary gland undergoes unique differentiative and proliferative development during the various life cycle stages of an individual. Accordingly, it should be understood that reference to mammary cells is a reference to the epithelial cells comprising the mammary gland at any stage of its development including prepubescent, pubescent, prenatal, postnatal/lactating and post-menopausal stages. In this regard, it should also be understood that any given population of epithelial cells of interest may only be transiently present in the mammary gland, such as those which are generated during pregnancy for the purpose of facilitating lactation.

Accordingly, in another preferred embodiment the present invention contemplates a method for detecting an aberrant mammary cell in a subject or in a biological sample from said subject, said method comprising contacting mammary cells or mammary cell extracts from said subject or said biological sample with an immunointeractive molecule specific for LM04 or antigenic portion thereof and screening for the level of immunointeractive molecule-LM04 complex formation wherein an elevated presence of said complex relative to a normal mammary cell is indicative of an aberrant mammary cell.

Reference herein to "mammary" cells or tissues should also be understood to extend to both epithelial and non-epithelial cell tissues. Such tissue includes but is not limited to, mammary epithelial cells, stromal cell, the lactiferous duct, ampulla, glandular tissue, areola and nipple. The mammary gland is often referred to by alternative terms such as the "breast" in human. The terms "mammary" and "breast" are herein utilised interchangeably. Reference to "mammary cells" should also be understood to extend to variants and mutants of said mammary cells, in the same context as hereinbefore defined with respect to epithelial cells in general.

In a related aspect, the present invention provides a method for detecting an aberrant cell in a subject or in a biological sample from said subject, said method comprising screening the level of a transcription product of a gene encoding LM04 wherein an elevated level of said expression product compared to a normal cell is indicative of an aberrant cell.

Preferably said aberrant cell is one which is characteristic of central nervous system tumors, retinoblastoma, head and neck cancers (eg. squamous cell cancers), lung cancer (both small and non-small cell lung cancer), kidney cancers (eg. renal cell adenocarinoma), pancreatic neoplasias (eg. adenocarcinomas and islet cell tumors), colorectal cancer, cervical cancer, testicular cancer (eg. germ cell tumors), ovarian cancer (eg. ovarian epithelial cancer and ovarian germ cell tumors), lymphomas, leukemias, malignant melanomas, neuroendocrine tumors and carcinoid tumors In another preferred embodiment, there is provided a method for detecting an aberrant epithelial cell in a subject or in a biological sample from said subject, said method comprising screening the level of a transcription product of a gene encoding LM04 wherein an elevated level of said expression product compared to a normal epithelial cell is indicative of an aberrant epithelial cell.

In yet another preferred embodiment, there is provided a method for detecting an aberrant mammary cell in a subject or in a biological sample from said subject, said method comprising screening the level of a transcription product of a gene encoding LM04 wherein an elevated level of said expression product compared to a normal mammary cell is indicative of an aberrant mammary cell.

Reference to "biological sample" should be understood as a reference to any sample of biological material derived from an individual such, but not limited to, mucus, stool, urine, blood, serum, cell extract, biopsy specimens and fluid which has been introduced into the body of an individual and subsequently removed such as, for example, the saline solution extracted from the lung following lung lavage or the solution retrieved from an enema wash. The biological sample which is tested according to the method of the present invention may be tested directly or may require some form of treatment prior to testing. For example, a biopsy sample may require homogenisation or sectioning prior to testing. Alternatively, the sample may require treatment in order to expose nucleic acid material.

Reference to a "normal" cell includes a cell not regarded as aberrant or cancerous and may be considered an "average" of normal cell types.

The "immunointeractive molecule" is any molecule having specificity and binding affinity for LM04 or its antigenic parts or its homologues or derivatives. Although the preferred immmunointeractive molecule is an immunglobulin molecule, the present invention extends to other immunointeractive molecules such as antibody fragments, single chain antibodies, deimmunized including humanized antibodies and T-cell associated antigen-binding molecules (TABMs). Most preferably, the immunointeractive molecule is an antibody such as a polyclonal or monoclonal antibody. It should be understood that the subject immunointeractive molecule may be limited, bound or otherwise associated to any other proteinaceous or non-proteinaceous molecule or cell. Most preferably, the antibody is a monoclonal antibody.

The immunointeractive molecule exhibits specificity for LM04 or more particularly an antigenic determinant or epitope on LM04. An antigenic determinant or epitope on LM04 includes that part of the molecule to which an immune response can be directed. The antigenic determinant or epitope may be a B-cell epitope or where appropriate a T-cell receptor binding molecule. The term "antigenic part" includes an antigenic determinant or epitope.

A "transcription product" is generally mRNA, although the present invention should also be understood to extend to cDNA which is reverse transcribed from all or part of an mRNA molecule. The amount of transcription product provides an indicator of the level of LM04 gene expression and provides, therefore, indirect evidence for the presence of LM04. Conveniently, pools of mRNA or cDNA are obtained or cell extracts comprising total mRNA obtained and genetic probes complementary to all or part of the LM04 gene-specific mRNA or cDNA. Binding of probes may then be quantitative or semi-quantitative.

Reference herein to LM04 includes reference to all forms of LM04 or their homologues or derivatives. Reference to "LM04" should be understood to include reference to any isoforms which arise from alternative splicing of LM04 mRNA or mutants or polymorphic variants of LM04. It should also be understood to include reference to any other molecule which exhibits LM04 functional activity to the extent that the subject molecule mimics one or more LM04 cellular proliferation related activities. It is conceivable, for example, that there may be naturally or non-naturally occurring LM04 mimetics (for example, toxins or drugs) which, if they were introduced into an individual, would induce unwanted cellular proliferation. Reference to "LM04" in italicised text should be understood as a reference to LM04 encoding nucleic acid molecules while "LM04" in not italicised text is a reference to the LM04 protein.

Reference to a "level" of LM04 includes an amount quantitatively, semi-quantitatively or qualitatively determined.

In accordance with the present invention, it is proposed that cells associated with a neoplasm, including malignant or non-malignant neoplastic cells, and in particular epithelial cancer cells or mammary cells, produce elevated levels of LM04. The quantitative or qualitative detection of levels of LM04 or expression products of genetic material encoding LM04 provides, therefore, an indicator that a cell is aberrant and is associated with neoplasia or has a propensity to develop into a neoplasia.

Reference herein to a "subject" should be understood to encompass humans, primates, livestock animals (eg. sheep, pigs, cattle, horses, donkeys), laboratory test animals (eg. mice, rabbits, rats, guinea pigs), companion animals (eg. dogs, cats) and captive wild animals (eg. foxes, kangaroos, deer). Preferably, the mammal is a human.

Accordingly, another aspect of the present invention contemplates a method for diagnosing the presence of a neoplasm or neoplasm-like growth in a subject, said method comprising contacting cells or cell extracts from said subject or a biological sample from said subject with a LM04-binding effective amount of an antibody having specificity for said LM04 or an antigenic determinant or epitope thereon and then quantitatively or qualitatively determining the level of a LM04-antibody complex wherein the presence of elevated levels of said complex compared to a normal cell is indicative of the presence of a neoplasm.

Preferably said neoplastic cell is one which is characteristic of central nervous system tumors, retinoblastoma, head and neck cancers (eg. squamous cell cancers), lung cancer (both small and non-small cell lung cancer), kidney cancers (eg. renal cell adenocarcinoma), pancreatic neoplasias (eg. adenocarcinomas and islet cell tumors), colorectal cancer, cervical cancer, testicular cancer (eg. germ cell tumors), ovarian cancer (eg. ovarian epithelial cancer and ovarian germ cell tumors), lymphomas, leukemias, malignant melanomas, neuroendocrine tumors and carcinoid tumors More preferably, said neoplasm is an epithelial cell neoplasm or a mammary cell neoplasm.

Most particularly, said mammary cell neoplasm is mammary-cell cancer.

In a related embodiment, the present invention provides a method for diagnosing the presence of a neoplasm in a subject, said method comprising obtaining mRNA from cells of said subject or from a biological sample from said subject and optionally generating cDNA and contacting said mRNA or cDNA with a genetic probe capable of hybridizing to and/or amplifying all or part of a nucleotide sequence encoding LM04 or its complementary nucleotide sequence and then detecting the level of said mRNA or cDNA wherein the presence of elevated levels of said mRNA or cDNA compared to normal controls is indicative of the presence of a neoplasm.

Preferably said neoplasm is central nervous system tumors, retinoblastoma, head and neck cancers (eg. squamous cell cancers), lung cancer (both small and non-small cell lung cancer), kidney cancers (eg. renal cell adenocarcinoma), pancreatic neoplasias (eg. adenocarcinomas and islet cell tumors), colorectal cancer, cervical cancer, testicular cancer (eg. germ cell tumors), ovarian cancer (eg. ovarian epithelial cancer and ovarian germ cell tumors), lymphomas, leukemias, malignant melanomas, neuroendocrine tumors and carcinoid tumors More particularly, said neoplasm is an epithelial cell neoplasm or mammary cell neoplasm.

Most particularly, said mammary cell neoplasm is mammary cell cancer.

The use of antibodies and in particular monoclonal antibodies to detect LM04 is a preferred method of the present invention. Antibodies may be prepared by any of a number of means. For the detection of human LM04, antibodies are generally but not necessarily derived from non-human animals such as primates, livestock animals (e.g. sheep, cows, pigs, goats, horses), laboratory test animals (e.g. mice, rats, guinea pigs, rabbits) and companion animals (e.g. dogs, cats). Generally, antibody based assays are conducted in vitro on cell or tissue biopsies. However, if an antibody is suitably deimmunized or, in the case of human use, humanized, then the antibody can be labelled with, for example, a nuclear tag, administered to a patient and the site of nuclear label accumulation determined by radiological techniques. The LM04 antibody is regarded, therefore, as a cancer targeting agent. Accordingly, the present invention extends to deimmunized forms of the antibodies for use in cancer imaging in human and non-human patients. This is described further below.

The present invention provides, therefore, an antibody and in particular a monoclonal antibody for use in immunological assays for LM04 or for cancer imaging in vivo. The antibody may be directed either to the LM04 protein or the LM04 mRNA, for example.

For the generation of antibodies to a LM04, this molecule is required to be extracted from a biological sample whether this be from animal including human tissue or from cell culture if produced by recombinant means. The LM04 can be separated from the biological sample by any suitable means. For example, the separation may take advantage of any one or more of LM04's surface charge properties, size, density, biological activity and its affinity for another entity (e.g. another protein or chemical compound to which it binds or otherwise associates). Thus, for example, separation of LM04 from the biological fluid may be achieved by any one or more of ultra-centrifugation, ion-exchange chromatography (e.g. anion exchange chromatography, cation exchange chromatography), electrophoresis (e.g. polyacrylamide gel electrophoresis, isoelectric focussing), size separation (e.g., gel filtration, ultra-filtration) and affinity-mediated separation (e.g. immunoaffinity separation including, but not limited to, magnetic bead separation such as Dynabead™ separation, immunochromatography, immuno-precipitation). Choice of the separation technique(s) employed may depend on the biological activity or physical properties of the LM04 sought or from which tissues it is obtained.

Preferably, the separation of LM04 from the biological fluid preserves conformational epitopes present on the protein and, thus, suitably avoids techniques that cause denaturation of the enzyme. Persons of skill in the art will recognize the importance of maintaining or mimicking as close as possible physiological conditions peculiar to the LM04 (e.g. the biological fluid from which it is obtained) to ensure that the antigenic determinants or active site/s on the LM04, which are exposed to the animal, are structurally identical to that of the native protein. This ensures the raising of appropriate antibodies in the immunised animal that would recognize the native protein. In a preferred embodiment, LM04 is separated from the biological fluid using any one or more of affinity separation, gel filtration and ultra-filtration.

Immunization and subsequent production of monoclonal antibodies can be carried out using standard protocols as for example described by Köhler and Milstein (1975, 1976), Coligan et al. (1991-1997) or Toyama et al. (1987). Essentially, an animal is immunized with a LM04-containing biological fluid or fraction thereof by standard methods to produce antibody-producing cells, particularly antibody-producing somatic cells (e.g. B lymphocytes). These cells can then be removed from the immunized animal for immortalization.

Where a fragment of LM04 is used to generate antibodies, it may need to first be associated with a carrier. By "carrier" is meant any substance of typically high molecular weight to which a non- or poorly immunogenic substance (e.g. a hapten) is naturally or artificially linked to enhance its immunogenicity.

Immortalization of antibody-producing cells may be carried out using methods which are well-known in the art. For example, the immortalization may be achieved by the transformation method using Epstein-Barr virus (EBV) (Kozbor et al., 1986). In a preferred embodiment, antibody-producing cells are immortalized using the cell fusion method (described in (Coligan et al., 1991-1997)), which is widely employed for the production of monoclonal antibodies. In this method, somatic antibody-producing cells with the potential to produce antibodies, particularly B cells, are fused with a myeloma cell line. These somatic cells may be derived from the lymph nodes, spleens and peripheral blood of primed animals, preferably rodent animals such as mice and rats. Mice spleen cells are particularly useful. It would be possible, however, to use rat, rabbit, sheep or goat cells, or cells from other animal species instead.

Specialized myeloma cell lines have been developed from lymphocytic tumours for use in hybridoma-producing fusion procedures (Kohler and Milstein, 1976; Shulman et al, 1978; Volk et al., 1982). These cell lines have been developed for at least three reasons. The first is to facilitate the selection of fused hybridomas from unfused and similarly indefinitely self-propagating myeloma cells. Usually, this is accomplished by using myelomas with enzyme deficiencies that render them incapable of growing in certain selective media that support the growth of hybridomas. The second reason arises from the inherent ability of lymphocytic tumour cells to produce their own antibodies. To eliminate the production of tumour cell antibodies by the hybridomas, myeloma cell lines incapable of producing endogenous light or heavy immunoglobulin chains are used. A third reason for selection of these cell lines is for their suitability and efficiency for fusion.

Many myeloma cell lines may be used for the production of fused cell hybrids, including, e.g. P3X63-Ag8, P3X63-AG8.653, P3/NS1-Ag4-1 (NS-1), Sp2/0-Ag14 and S194/5.XXO.Bu.1. The P3X63-Ag8 and NS-1 cell lines have been described by Köhler and Milstein (1976). Shulman et al. (1978) developed the Sp2/0-Ag14 myeloma line. The S194/5.XXO.Bu.1 line was reported by Trowbridge (1978).

Methods for generating hybrids of antibody-producing spleen or lymph node cells and myeloma cells usually involve mixing somatic cells with myeloma cells in a 10:1 proportion (although the proportion may vary from about 20:1 to about 1:1), respectively, in the presence of an agent or agents (chemical, viral or electrical) that promotes the fusion of cell membranes. Fusion methods have been described (Kohler and Milstein, 1975; 1976; Gafter et al., 1977; Volk et al., 1982). The fusion-promoting agents used by those investigators were Sendai virus and polyethylene glycol (PEG).

Because fusion procedures produce viable hybrids at very low frequency (e.g. when spleens are used as a source of somatic cells, only one hybrid is obtained for roughly every $1 \times 10^5$ spleen cells), it is preferable to have a means of selecting the fused cell hybrids from the remaining unfused cells, particularly the unfused myeloma cells. A means of detecting the desired antibody-producing hybridomas among other resulting fused cell hybrids is also necessary. Generally, the selection of fused cell hybrids is accomplished by culturing the cells in media that support the growth of hybridomas but prevent the growth of the unfused myeloma cells, which normally would go on dividing indefinitely. The somatic cells used in the fusion do not maintain long-term viability in in vitro culture and hence do not pose a problem. In the example of the present invention, myeloma cells lacking hypoxanthine phosphoribosyl transferase (HPRT-negative) were used. Selection against these cells is made in hypoxanthine/aminopterin/thymidine (HAT) medium, a medium in which the fused cell hybrids survive due to the HPRT-positive genotype of the spleen cells. The use of myeloma cells with different genetic deficiencies (drug sensitivities, etc.) that can be selected against in media supporting the growth of genotypically competent hybrids is also possible.

Several weeks are required to selectively culture the fused cell hybrids. Early in this time period, it is necessary to identify those hybrids which produce the desired antibody, so that they may subsequently be cloned and propagated. Generally, around 10% of the hybrids obtained produce the desired antibody, although a range of from about 1 to about 30% is not uncommon. The detection of antibody-producing hybrids can be achieved by any one of several standard assay methods, including enzyme-linked immunoassay and radioimmunoassay techniques as, for example, described in Kennet et al. (1980) and by FACS analysis (1998).

Once the desired fused cell hybrids have been selected and cloned into individual antibody-producing cell lines, each cell line may be propagated in either of two standard ways. A suspension of the hybridoma cells can be injected into a histocompatible animal. The injected animal will then develop tumours that secrete the specific monoclonal antibody produced by the fused cell hybrid. The body fluids of the animal, such as serum or ascites fluid, can be tapped to provide monoclonal antibodies in high concentration. Alternatively, the individual cell lines may be propagated in vitro in laboratory culture vessels. The culture medium containing high concentrations of a single specific monoclonal antibody can be harvested by decantation, filtration or centrifugation, and subsequently purified.

The cell lines are tested for their specificity to detect the LM04 by any suitable immunodetection means. For example, cell lines can be aliquoted into a number of wells and incubated and the supernatant from each well is analyzed by enzyme-linked immunosorbent assay (ELISA), indirect fluorescent antibody technique, or the like. The cell line(s) producing a monoclonal antibody capable of recognizing the target LM04 but which does not recognize non-target epitopes are identified and then directly cultured in vitro or injected into a histocompatible animal to form tumours and to produce, collect and purify the required antibodies.

These antibodies are LM04 specific. This means that the antibodies are capable of distinguishing LM04 from other molecules. More broad spectrum antibodies may be used provided that they do not cross react with molecules in a normal cell.

In a preferred embodiment, the subject antibody is 16H2 or 20F8 or derivative, homologue, analogue, chemical equivalent, mutant or mimetic thereof.

Hybridoma cell lines secreting 16H2 and 20F8 were deposited with European Collection of Cell Cultures (ECACC), CAMR, Salisbury. Wiltshire SP4, OJG, United Kingdom, under accession numbers 03052001 and 03052002, respectively, on May 20, 2003.

The present invention should also be understood to extend to the cell lines which express the subject immunointeractive molecule, in particular a hybridoma which expresses a monoclonal antibody. Most preferably said hybridoma is the hybridoma cell line 16H2 or 20F8 or mutant or variant thereof.

Where the monoclonal antibody is destined for use in in vivo cancer imaging or treatment, it will need to be deimmunized with respect to the host into which it will be introduced (e.g. a human). The deimmunization process may take any of a number of forms including the preparation of chimeric antibodies which have the same or similar specificity as the monoclonal antibodies prepared according to the present invention. Chimeric antibodies are antibodies whose light and heavy chain genes have been constructed, typically by genetic engineering, from immunoglobulin variable and constant region genes belonging to different species. Thus, in accordance with the present invention, once a hybridoma producing the desired monoclonal antibody is obtained, techniques are used to produce interspecific monoclonal antibodies wherein the binding region of one species is combined with a non-binding region of the antibody of another species (Liu et al., 1987). For example, complementary determining regions (CDRs) from a non-human (e.g. murine) monoclonal antibody can be grafted onto a human antibody, thereby "humanizing" the murine antibody (European Patent Publication No. 0 239 400; Jones et al., 1986; Verhoeyen et al., 1988; Richmann et al., 1988). In this case, the deimmunizing process is specific for humans. More particularly, the CDRs can be grafted onto a human antibody variable region with or without human constant regions. The non-human antibody providing the CDRs is typically referred to as the "donor" and the human antibody providing the framework is typically referred to as the "acceptor". Constant regions need not be present, but if they are, they must be substantially identical to human immunoglobulin constant regions, i.e. at least about 85-90%, preferably about 95% or more identical. Hence, all parts of a humanized antibody, except possibly the CDRs, are substantially identical to corresponding parts of natural human immunoglobulin sequences. Thus, a "humanized antibody" is an antibody comprising a humanized light chain and a humanized heavy chain immunoglobulin. A donor antibody is said to be "humanized", by the process of "humanization", because the resultant humanized antibody is expected to bind to the same antigen as the donor antibody that provides the CDRs. Reference herein to "humanized" includes reference to an antibody deimmunized to a particular host, in this case, a human host.

It will be understood that the deimmunized antibodies may have additional conservative amino acid substitutions which have substantially no effect on antigen binding or other immunoglobulin functions. Exemplary conservative substitutions may be made according to Table 1.

TABLE 1

| ORIGINAL RESIDUE | EXEMPLARY SUBSTITUTIONS |
|---|---|
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Exemplary methods which may be employed to produce deimmunized antibodies according to the present invention are described, for example, in references Richmann et al., 1988; European Patent Publication No. 0 239 400; Chou et al; Queen et al; Morgan et al.

Thus, in one embodiment, the present invention contemplates a deimmunized antibody molecule having specificity for an epitope recognized by a monoclonal antibody to LM04 wherein at least one of the CDRs of the variable domain of said deimmunized antibody is derived from the said monoclonal antibody to LM04 and the remaining immunoglobulin-derived parts of the deimmunized antibody molecule are derived from an immunoglobulin or an analogue thereof from the host for which the antibody is to be deimmunized.

This aspect of the present invention involves manipulation of the framework region of a non-human antibody.

The present invention extends to mutants, analogues and derivatives of the subject antibodies but which still retain specificity for LM04.

The terms "mutant" or "derivatives" includes one or more amino acid substitutions, additions and/or deletions.

As used herein, the term "CDR" includes CDR structural loops which covers the three light chain and the three heavy chain regions in the variable portion of an antibody framework region which bridge m strands on the binding portion of the molecule. These loops have characteristic canonical structures (Chothia et al., 1987; Chothia et al., 1992).

By "framework region" is meant region of an immunoglobulin light or heavy chain variable region, which is interrupted by three hypervariable regions, also called CDRs. The extent of the framework region and CDRs have been precisely defined (see, for example, Kabat et al., 1983). The sequences of the framework regions of different light or heavy chains are relatively conserved within a species. As used herein, a "human framework region" is a framework region that is substantially identical (about 85% or more, usually 90-95% or more) to the framework region of a naturally occurring human immunoglobulin. The framework region of an antibody, that is the combined framework regions of the constituent light and heavy chains, serves to position and align the CDRs. The CDRs are primarily responsible for binding to an epitope of LM04.

As used herein, the term "heavy chain variable region" means a polypeptide which is from about 110 to 125 amino acid residues in length, the amino acid sequence of which corresponds to that of a heavy chain of a monoclonal antibody of the invention, starting from the amino-terminal (N-terminal) amino acid residue of the heavy chain. Likewise, the term "light chain variable region" means a polypeptide which is from about 95 to 130 amino acid residues in length, the amino acid sequence of which corresponds to that of a light chain of a monoclonal antibody of the invention, starting from the N-terminal amino acid residue of the light chain. Full-length immunoglobulin "light chains" (about 25 Kd or 214 amino acids) are encoded by a variable region gene at the $NH_2$-terminus (about 110 amino acids) and a κ or λ constant region gene at the COOH-terminus. Full-length immunoglobulin "heavy chains" (about 50 Kd or 446 amino acids), are similarly encoded by a variable region gene (about 116 amino acids) and one of the other aforementioned constant region genes, e.g. γ (encoding about 330 amino acids).

The term "immunoglobulin" or "antibody" is used herein to refer to a protein consisting of one or more polypeptides substantially encoded by immunoglobulin genes. The recognized immunoglobulin genes include the κ, λ, α, γ ($IgG_1$, $IgG_2$, $IgG_3$, $IgG_4$), δ, ε and μ constant region genes, as well as the myriad immunoglobulin variable region genes. One form of immunoglobulin constitutes the basic structural unit of an antibody. This form is a tetramer and consists of two identical pairs of immunoglobulin chains, each pair having one light and one heavy chain. In each pair, the light and heavy chain variable regions are together responsible for binding to an antigen, and the constant regions are responsible for the antibody effector functions. In addition to antibodies, immunoglobulins may exist in a variety of other forms including, for example, Fv, Fab, Fab' and $(Fab')_2$.

The invention also contemplates the use and generation of fragments of monoclonal antibodies produced by the method of the present invention including, for example, Fv, Fab, Fab' and $F(ab')_2$ fragments. Such fragments may be prepared by standard methods as for example described by Coligan et al. (1991-1997).

The present invention also contemplates synthetic or recombinant antigen-binding molecules with the same or similar specificity as the monoclonal antibodies of the invention. Antigen-binding molecules of this type may comprise a synthetic stabilised Fv fragment. Exemplary fragments of this type include single chain Fv fragments (sFv, frequently termed scFv) in which a peptide linker is used to bridge the N terminus or C terminus of a $V_H$ domain with the C terminus or N-terminus, respectively, of a $V_L$ domain. ScFv lack all constant parts of whole antibodies and are not able to activate complement. Suitable peptide linkers for joining the $V_H$ and $V_L$ domains are those which allow the $V_H$ and $V_L$ domains to fold into a single polypeptide chain having an antigen binding site with a three dimensional structure similar to that of the antigen binding site of a whole antibody from which the Fv fragment is derived. Linkers having the desired properties may be obtained by the method disclosed in U.S. Pat. No. 4,946,778. However, in some cases a linker is absent. ScFvs may be prepared, for example, in accordance with methods outlined in Krebber et al. (Krebber et al., 1997). Alternatively, they may be prepared by methods described in U.S. Pat. No. 5,091,513, European Patent No 239,400 or the articles by Winter and Milstein (Winter and Milstein, 1991) and Pluckthum et al. (Pluckthum et al., 1996).

Alternatively, the synthetic stabilized Fv fragment comprises a disulphide stabilized Fv (dsFv) in which cysteine residues are introduced into the $V_H$ and $V_L$ domains such that in the fully folded Fv molecule the two residues will form a disulphide bond therebetween. Suitable methods of producing dsFv are described, for example, in (Glockshuber et al., 1990; Reiter et al., 1994; Reiter et al., 1994; Reiter et al., 1994; Webber et al., 1995).

Also contemplated as synthetic or recombinant antigen-binding molecules are single variable region domains (termed dAbs) as, for example, disclosed in (Ward et al., 1989; Hamers-Casterman et al., 1993; Davies & Reichmann, 1994).

Alternatively, the synthetic or recombinant antigen-binding molecule may comprise a "minibody". In this regard, minibodies are small versions of whole antibodies, which encode in a single chain the essential elements of a whole antibody. Suitably, the minibody is comprised of the $V_H$ and $V_L$ domains of a native antibody fused to the hinge region and CH3 domain of the immunoglobulin molecule as, for example, disclosed in U.S. Pat. No. 5,837,821.

In an alternate embodiment, the synthetic or recombinant antigen binding molecule may comprise non-immunoglobulin derived, protein frameworks. For example, reference may be made to (Ku & Schutz, 1995) which discloses a four-helix bundle protein cytochrome b562 having two loops randomized to create CDRs, which have been selected for antigen binding.

The synthetic or recombinant antigen-binding molecule may be multivalent (i.e. having more than one antigen binding site). Such multivalent molecules may be specific for one or more antigens. Multivalent molecules of this type may be prepared by dimerization of two antibody fragments through a cysteinyl-containing peptide as, for example disclosed by (Adams et al., 1993; Cumber et al., 1992). Alternatively, dimerization may be facilitated by fusion of the antibody fragments to amphiphilic helices that naturally dimerize (Pluckthum, 1992) or by use of domains (such as leucine zippers jun and fos) that preferentially heterodimerize (Kostelny et al., 1992).

The present invention further encompasses chemical analogues of amino acids in the subject antibodies. The use of chemical analogues of amino acids is useful inter alia to stabilize the molecules such as if required to be administered to a subject. The analogues of the amino acids contemplated herein include, but are not limited to, modifications of side chains, incorporation of unnatural amino acids and/or their derivatives during peptide, polypeptide or protein synthesis and the use of crosslinkers and other methods which impose conformational constraints on the proteinaceous molecule or their analogues.

Examples of side chain modifications contemplated by the present invention include modifications of amino groups such as by reductive alkylation by reaction with an aldehyde followed by reduction with $NaBH_4$; amidination with methylacetimidate; acylation with acetic anhydride; carbamoylation of amino groups with cyanate; trinitrobenzylation of amino groups with 2,4,6-trinitrobenzene sulphonic acid (TNBS); acylation of amino groups with succinic anhydride and tetrahydrophthalic anhydride; and pyridoxylation of lysine with pyridoxal-5-phosphate followed by reduction with $NaBH_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitisation, for example, to a corresponding amide. Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids. A list of unnatural amino acid, contemplated herein is shown in Table 2.

TABLE 2

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-Nmethylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcylcopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cylcododecylglycine | Ncdod |
| D-N-methylalanine | Dnmala | N-cyclooctylglycine | Ncoct |
| D-N-methylarginine | Dnmarg | N-cyclopropylglycine | Ncpro |
| D-N-methylasparagine | Dnmasn | N-cycloundecylglycine | Ncund |
| D-N-methylaspartate | Dnmasp | N-(2,2-diphenylethyl)glycine | Nbhm |
| D-N-methylcysteine | Dnmcys | N-(3,3-diphenylpropyl)glycine | Nbhe |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl))glycine | Nser |
| D-N-methylisoleucine | Dnmile | N-(imidazolylethyl))glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |

TABLE 2-continued

| Non-conventional amino acid | Code | Non-conventional amino acid | Code |
|---|---|---|---|
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | Mser | L-α-methylthreonine | Mthr |
| L-α-methyltryptophan | Mtrp | L-α-methyltyrosine | Mtyr |
| L-α-methylvaline | Mval | L-N-methylhomophenylalanine | Nmhphe |
| N-(N-(2,2-diphenylethyl) carbamylmethyl)glycine | Nnbhm | N-(N-(3,3-diphenylpropyl) carbamylmethyl)glycine | Nnbhe |
| 1-carboxy-1-(2,2-diphenyl-ethylamino)cyclopropane | Nmbc | | |

Crosslinkers can be used, for example, to stabilize 3D conformations, using homo-bifunctional crosslinkers such as the bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio moiety (SH) or carbodiimide (COOH). In addition, peptides can be conformationally constrained by, for example, incorporation of $C_\alpha$ and $N_\alpha$-methylamino acids, introduction of double bonds between $C_\alpha$ and $C_\beta$ atoms of amino acids and the formation of cyclic peptides or analogues by introducing covalent bonds such as forming an amide bond between the N and C termini, between two side chains or between a side chain and the N or C terminus.

The present invention further contemplates an assay to detect LM04 including the steps of:—

(3) contacting a monoclonal antibody specific to LM04 or an antigenic determinant thereon with a biological sample suspected of containing a cell containing said LM04; and (4) subjecting the complex formed in step (1) to a signal detection step.

The signal detection step may include ELISA or any other reporter molecule based assays. As part of this detection step, the signal may first need to be amplified.

A deimmunized monoclonal antibody of the present invention may also be useful for cancer imaging in vivo as well as for targeting cancer cells in order to bring the cancer cells into contact with cell growth retarding or cell killing agents, i.e. cytostatic or cytocidal agents.

With respect to cancer imaging, a reporter molecule is attached to the deimmunized monoclonal antibody and this is then introduced to a host, such as a human. By detecting the reporter molecule, cancer growths can be visualized. One particularly useful form of reporter molecule is a nuclear tag.

Accordingly, another aspect of the present invention contemplates a method for detecting neoplastic cells in a human patient, said method comprising introducing into said patient a deimmunized form of a non-human derived monoclonal antibody specific for human LM04 or an antigenic determinant thereon labelled with a reporter molecule, allowing dissemination of the labelled antibody throughout the circulatory system, or to selected parts of the circulatory system and then subjecting said patient to reporter molecule-detection means to identify the location of the antibody.

Preferably said neoplastic cell is one which is characteristic of central nervous system tumors, retinoblastoma, head and neck cancers (eg. squamous cell cancers), lung cancer (both small and non-small cell lung cancer), kidney cancers (eg. renal cell adenocarcinoma), pancreatic neoplasias (eg. adenocarcinomas and islet cell tumors), colorectal cancer, cervical cancer, testicular cancer (eg. germ cell tumors), ovarian cancer (eg. ovarian epithelial cancer and ovarian germ cell tumors), lymphomas, leukemias, malignant melanomas, neuroendocrine tumors and carcinoid tumors Preferably, said neoplastic cells are neoplastic epithelial cells or neoplastic mammary cells. More particularly, said neoplastic mammary cells are malignant mammary cells.

Immunological based LM04 detection protocols may take a variety of forms. For example, a plurality of antibodies may be immobilized in an array each with different specificities to particular antigens or cancer cells including LM04. Cells from a biopsy are then brought into contact with the antibody array and a diagnosis may be made as to the type of cancer based on the cells which are immobilized.

Other more conventional assays may also be conducted such as by ELISA, Western blot analysis, immunoprecipitation analysis, immunofluorescence analysis, immunochemistry analysis or FACS analysis.

The present invention provides, therefore, a method of detecting, in a sample, LM04 or fragment, variant or derivative thereof comprising contacting the sample with an antibody or fragment or derivative thereof and detecting the level of a complex comprising said antibody and LM04 or fragment, variant or derivative thereof compared to normal controls wherein elevated levels of LM04 is indicative of cancer growth.

As discussed above, any suitable technique for determining formation of the complex may be used. For example, an antibody according to the invention, having a reporter molecule associated therewith, may be utilized in immunoassays. Such immunoassays include but are not limited to radioimmunoassays (RIAs), enzyme-linked immunosorbent assays (ELISAs) and immunochromatographic techniques (ICTs), Western blotting which are well known to those of skill in the art. For example, reference may be made to "Current Protocols in Immunology", 1994 which discloses a variety of immunoassays which may be used in accordance with the present invention. Immunoassays may include competitive assays. It will be understood that the present invention encompasses qualitative and quantitative immunoassays.

Suitable immunoassay techniques are described, for example, in U.S. Pat. Nos. 4,016,043, 4,424,279 and 4,018,653. These include both single-site and two-site assays of the non-competitive types, as well as the traditional competitive binding assays. These assays also include direct binding of a labelled antigen-binding molecule to a target antigen. The antigen in this case is LM04 or a fragment thereof.

Two-site assays are particularly favoured for use in the present invention. A number of variations of these assays exist, all of which are intended to be encompassed by the present invention. Briefly, in a typical forward assay, an unlabelled antigen-binding molecule such as an unlabelled antibody is immobilized on a solid substrate and the sample to be tested brought into contact with the bound molecule. After a suitable period of incubation, for a period of time sufficient to allow formation of an antibody-antigen complex, another antigen-binding molecule, suitably a second antibody specific to the antigen, labelled with a reporter molecule capable of producing a detectable signal is then added and incubated, allowing time sufficient for the formation of another complex of antibody-antigen-labelled antibody. Any unreacted material is washed away and the presence of the antigen is determined by observation of a signal produced by the reporter molecule. The results may be either qualitative, by simple observation of the visible signal, or may be quantitated by comparing with a control sample containing known amounts of antigen. Variations on the forward assay include a simultaneous assay, in which both sample and labelled antibody are added simultaneously to the bound antibody. These techniques are well known to those skilled in the art, including minor variations as will be readily apparent.

In the typical forward assay, a first antibody having specificity for the antigen or antigenic parts thereof is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, discs of microplates, or any other surface suitable for conducting an immunoassay. The binding processes are well known in the art and generally consist of cross-linking covalently binding or physically adsorbing, the polymer-antibody complex is washed in preparation for the test sample. An aliquot of the sample to be tested is then added to the solid phase complex and incubated for a period of time sufficient and under suitable conditions to allow binding of any antigen present to the antibody. Following the incubation period, the antigen-antibody complex is washed and dried and incubated with a second antibody specific for a portion of the antigen. The second antibody has generally a reporter molecule associated therewith that is used to indicate the binding of the second antibody to the antigen. The amount of labelled antibody that binds, as determined by the associated reporter molecule, is proportional to the amount of antigen bound to the immobilized first antibody.

An alternative method involves immobilizing the antigen in the biological sample and then exposing the immobilized antigen to specific antibody that may or may not be labelled with a reporter molecule. Depending on the amount of target and the strength of the reporter molecule signal, a bound antigen may be detectable by direct labelling with the antibody. Alternatively, a second labelled antibody, specific to the first antibody is exposed to the target-first antibody complex to form a target-first antibody-second antibody tertiary complex. The complex is detected by the signal emitted by the reporter molecule.

From the foregoing, it will be appreciated that the reporter molecule associated with the antigen-binding molecule may include the following:—
 (a) direct attachment of the reporter molecule to the antibody;
 (b) indirect attachment of the reporter molecule to the antibody; i.e., attachment of the reporter molecule to another assay reagent which subsequently binds to the antibody; and
 (c) attachment to a subsequent reaction product of the antibody.

The reporter molecule may be selected from a group including a chromogen, a catalyst, an enzyme, a fluorochrome, a chemiluminescent molecule, a paramagnetic ion, a lanthanide ion such as Europium ($Eu^{34}$), a radioisotope including other nuclear tags and a direct visual label.

In the case of a direct visual label, use may be made of a colloidal metallic or non-metallic particle, a dye particle, an enzyme or a substrate, an organic polymer, a latex particle, a liposome, or other vesicle containing a signal producing substance and the like.

A large number of enzymes suitable for use as reporter molecules is disclosed in U.S. Pat. No. 4,366,241, U.S. Pat. No. 4,843,000, and U.S. Pat. No. 4,849,338. Suitable enzymes useful in the present invention include alkaline phosphatase, horseradish peroxidase, luciferase, β-galactosidase, glucose oxidase, lysozyme, malate dehydrogenase and the like. The enzymes may be used alone or in combination with a second enzyme that is in solution.

Suitable fluorochromes include, but are not limited to, fluorescein isothiocyanate (FITC), tetramethylrhodamine isothiocyanate (TRITC), R-Phycoerythrin (RPE), and Texas Red. Other exemplary fluorochromes include those discussed by Dower et al., International Publication No. WO 93/06121. Reference also may be made to the fluorochromes described in U.S. Pat. Nos. 5,573,909 (Singer et al), 5,326,692 (Brinkley et al). Alternatively, reference may be made to the fluorochromes described in U.S. Pat. Nos. 5,227,487, 5,274,113, 5,405,975, 5,433,896, 5,442,045, 5,451,663, 5,453,517, 5,459,276, 5,516,864, 5,648,270 and 5,723,218.

In the case of an enzyme immunoassay, an enzyme is conjugated to the second antibody, generally by means of glutaraldehyde or periodate. As will be readily recognized, however, a wide variety of different conjugation techniques exist which are readily available to the skilled artisan. The substrates to be used with the specific enzymes are generally chosen for the production of, upon hydrolysis by the corresponding enzyme, a detectable colour change. Examples of suitable enzymes include those described supra. It is also possible to employ fluorogenic substrates, which yield a fluorescent product rather than the chromogenic substrates noted above. In all cases, the enzyme-labelled antibody is added to the first antibody-antigen complex, allowed to bind, and then the excess reagent washed away. A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of antigen which was present in the sample.

Alternately, fluorescent compounds, such as fluorescein, rhodamine and the lanthanide, europium (EU), may be chemically coupled to antibodies without altering their binding capacity. When activated by illumination with light of a particular wavelength, the fluorochrome-labelled antibody adsorbs the light energy, inducing a state to excitability in the molecule, followed by emission of the light at a characteristic colour visually detectable with a light microscope. The fluorescent-labelled antibody is allowed to bind to the first antibody-antigen complex. After washing off the unbound reagent, the remaining tertiary complex is then exposed to light of an appropriate wavelength. The fluorescence observed indicates the presence of the antigen of interest. Immunofluorometric assays (IFMA) are well established in the art and are particularly useful for the present method. However, other reporter molecules, such as radioisotope, chemiluminescent or bioluminescent molecules may also be employed.

In another embodiment, the method for detection comprises detecting the level of expression in a cell of a polynucleotide encoding a LM04. Expression of said polynucleotide may be determined using any suitable technique. For example, a labelled polynucleotide encoding a LM04 may be utilized as a probe in a Northern blot of an RNA extract obtained from the cell. Preferably, a nucleic acid extract from the animal is utilized in concert with oligonucleotide primers corresponding to sense and antisense sequences of a polynucleotide encoding the kinase, or flanking sequences thereof, in a nucleic acid amplification reaction such as RT PCR, real time PCR or SAGE. A variety of automated solid-phase detection techniques are also appropriate. For example, a very large scale immobilized primer arrays (VLSIPS™) are used for the detection of nucleic acids as, for example, described by Fodor et al., 1991 and Kazal et al., 1996. The above genetic techniques are well known to persons skilled in the art.

For example, to detect LM04 encoding RNA transcripts, RNA is isolated from a cellular sample suspected of containing LM04 RNA, e.g. total RNA isolated from human breast cancer tissue. RNA can be isolated by methods known in the art, e.g. using TRIZOL™ reagent (GIBCO-BRL/Life Technologies, Gaithersburg, Md.). Oligo-dT, or random-sequence oligonucleotides, as well as sequence-specific oligonucleotides can be employed as a primer in a reverse transcriptase reaction to prepare first-strand cDNAs from the isolated RNA. Resultant first-strand cDNAs are then amplified with sequence-specific oligonucleotides in PCR reactions to yield an amplified product.

"Polymerase chain reaction" or "PCR" refers to a procedure or technique in which amounts of a preselected fragment of nucleic acid, RNA and/or DNA, are amplified as described in U.S. Pat. No. 4,683,195. Generally, sequence information from the ends of the region of interest or beyond is employed to design oligonucleotide primers. These primers will be identical or similar in sequence to opposite strands of the template to be amplified. PCR can be used to amplify specific RNA sequences and cDNA transcribed from total cellular RNA. See generally Mullis et al., 1987; Erlich, 1989. Thus, amplification of specific nucleic acid sequences by PCR relies upon oligonucleotides or "primers" having conserved nucleotide sequences wherein the conserved sequences are deduced from alignments of related gene or protein sequences, e.g. a sequence comparison of mammalian LM04 genes. For example, one primer is prepared which is predicted to anneal to the antisense strand and another primer prepared which is predicted to anneal to the sense strand of a cDNA molecule which encodes LM04.

To detect the amplified product, the reaction mixture is typically subjected to agarose gel electrophoresis or other convenient separation technique and the relative presence of the LM04 specific amplified DNA detected. For example, LM04 amplified DNA may be detected using Southern hybridization with a specific oligonucleotide probe or comparing is electrophoretic mobility with DNA standards of known molecular weight. Isolation, purification and characterization of the amplified LM04 DNA may be accomplished by excising or eluting the fragment from the gel (for example, see references Lawn et al., 1981; Goeddel et al., 1980), cloning the amplified product into a cloning site of a suitable vector, such as the pCRII vector (Invitrogen), sequencing the cloned insert and comparing the DNA sequence to the known sequence of LM04. The relative amounts of LM04 mRNA and cDNA can then be determined.

The present invention may be used to detect any neoplasm which comprises cells which express elevated levels of LM04.

The method of the present invention is useful as a one off test or as an on-going monitor of those individuals thought to be at risk of neoplasm development or as a monitor of the effectiveness of therapeutic or prophylactic treatment regimes directed to inhibiting or otherwise slowing neoplasm development, in particular, epithelial cell cancers and most particularly breast cancer development. In these situation, mapping the modulation of LM04 levels in any one or more classes of biological samples is a valuable indicator of the status of an individual or the effectiveness of a therapeutic or prophylactic regime which is currently in use. Accordingly, the method of the present invention should be understood to extend to monitoring for increases or decreases in marker levels in an individual relative to their normal level (as hereinbefore defined) or relative to one or more earlier marker levels determined from a biological sample of said individual.

Accordingly, another aspect of the present invention provides a method of monitoring for the onset or progression of a neoplasm in a subject, said method comprising screening for the level of LM04 or a transcription product of a gene encoding LM04 in a biological sample from said subject wherein an elevated level of said LM04 or transcription product compared to the levels of a normal cell is indicative of a neoplasm.

The present invention further contemplates the use of a monoclonal antibody to LM04 in the manufacture of a quantitative or semi-quantitative diagnostic kit to determine relative levels of LM04 in suspected neoplastic cells from a patient. The kit may come with instructions for use and may be automated or semi-automated or in a form which is compatible with automated machine or software.

The generation of antibodies to LM04 may, in accordance with the present invention, be directed to the active or inactive forms of the molecule. Antibodies directed to an active LM04 are particularly useful in detecting an increase or decrease in LM04 activity.

The identification of LM04 as a cancer-specific molecule, in particular a breast cancer specific molecule, permits the generation of targeting agents to destroy or at least retard the growth of the cancer cells. In particular, the cancer targeting agents comprising LM04 specific antibodies are fused, bound or otherwise associated with a cell growth inhibiting or killing agent. Such agents include but are not limited to cytocidal or cytostatic agents which act at the protein or corresponding mRNA or DNA levels. For example, the cell growth or killing agent maybe a nuclear tag or may be an agent which promotes induction of antagonists of LM04 RNAi or RNA oligonucleotides.

Accordingly, one aspect of the present invention provides a method of modulating LM04 regulated cellular proliferation, said method comprising contacting said cell with an effective amount of an agent for a time and under conditions sufficient to modulate LM04 expression or LM04 functional activity wherein inhibiting or otherwise antagonising said expression or activity down-regulates said cellular proliferation.

Reference to "LM04 regulated cellular proliferation" should be understood as a reference to proliferative activity which is either directly or indirectly induced or otherwise regulated by LM04.

Without limiting the present invention to any one theoy or mode of action, up-regulation of LM04 expression has been identified as a marker of uncontrolled breast cell proliferation, in particular epithelial breast cell proliferation. However, it should be understood that the diagnostic, therapeutic and prophylactic methodology disclosed herein should not be limited to uncontrolled breast cell proliferation but extended to any cell type, the proliferation of which is directly or indirectly regulated by LM04.

The present invention more particularly provides a method of modulating LM04-regulated mammary cell proliferation, said method comprising contacting said cell with an effective amount of an agent for a time and under conditions sufficient to modulate LM04 expression or LM04 functional activity wherein inhibiting or otherwise antagonising said expression or activity down-regulates said cellular proliferation.

It should be understood that antagonism of LM04 expression or activity may be partial or complete. Partial modulation occurs where only some LM04 expression or activity occurring in a given cell is down-regulated. LM04 expression or functional activity is down-regulated.

Down-regulation of LM04 expression or LM04 functional activity may be achieved by any one of a number of techniques including, but not limited to:
  (i) introducing into a cell a proteinaceous or non-proteinaceous molecule which modulates the transcriptional and/or translational regulation of the LM04 gene or a gene, the expression product of which regulates LM04 expression.
  (ii) introducing into a cell a proteinaceous or non-proteinaceous molecule which antagonises the interaction between LM04 and one or more of its ligands (for example, bdb1, Nb1, CLIM, CtIP or BRCA1).

Up-regulation of LM04 may also be desired in certain circumstances and may be achieved by introducing into a cell, LM04, LM04 or derivative, chemical equivalent, homologue or mimetic thereof or a proteinaceous or non-proteinaceous molecule which agonises the interaction between LM04 and its ligands or otherwise upregulates its activity or LM04 expression.

Reference to "agent" should be understood as a reference to any proteinaceous or non-proteinaceous molecule which achieves the above objectives and includes, for example, the molecules detailed in the points above. The subject agent may be linked, bound or otherwise associated with any proteinaceous or non-proteinaceous molecule. For example, it may be associated with a molecule which permits its targeting to a localised region, for example the breast.

Said proteinaceous molecule may be derived from natural, recombinant or synthetic sources including fusion proteins or following, for example, natural product screening. Said non-proteinaceous molecule may be derived from natural sources, such as for example natural product screening or may be chemically synthesised. The present invention contemplates chemical analogues of said LM04 capable of acting as antagonists of LM04 interactions. Antagonists may be any compound capable of blocking, inhibiting or otherwise preventing said LM04 from interacting. Antagonists include monoclonal antibodies specific for said LM04, or parts of said LM04, and antisense nucleic acids which prevent transcription or translation of genes or mRNA in the subject cells.

Modulation of expression may also be achieved utilising antigens, RNA, ribosomes, DNAzymes, RNA aptamers, antibodies or molecules suitable for use in co-suppression or to induce RNAi-mediated down-regulation of LM04 mRNA transcript.

Synthetic sources of said agent include for example chemically synthesised molecules. In other examples, phage display libraries can be screened for peptides while chemical libraries can be screened for existing small molecules. Rational drug design/structure based design can be achieved by performing crystallisation, further analysing the LM04 binding sites and fitting molecules into that site by design.

For example chemical or functional equivalents of LM04 can be designed and/or identified utilising well known methods such as combinatorial chemistry or high throughput screening of recombinant libraries or following natural product screening.

In another example, libraries containing small organic molecules may be screened, wherein organic molecules having a large number of specific parent group substitutions are used. A general synthetic scheme may follow published methods (e.g. Bunin et al., 1994; DeWitt et al., 1993). Briefly, at each successive synthetic step, one of a plurality of different selected substituents is added to each of a selected subset of tubes in an array, with the selection of tube subsets being such as to generate all possible permutation of the different substituents employed in producing the library. One suitable permutation strategy is outlined in U.S. Pat. No. 5,763,263.

There is currently widespread interest in using combinational libraries of random organic molecules to search for biologically active compounds (see for example U.S. Pat. No. 5,763,263). Ligands discovered by screening libraries of this type may be useful in mimicking or blocking natural ligands or interfering with the naturally occurring ligands of a biological target. In the present context, for example, they may be used as a starting point for developing analogues which exhibit properties such as more potent pharmacological effects. LM04 or a functional part thereof may according to the present invention be used in combination libraries formed by various solid-phase or solution-phase synthetic methods (see for example U.S. Pat. No. 5,763,263 and references cited therein). By use of techniques, such as that disclosed in U.S. Pat. No. 5,753,187, millions of new chemical and/or biological compounds may be routinely screened in less than a few weeks. Of the large number of compounds identified, only those exhibiting appropriate biological activity are further analysed.

With respect to high throughput library screening methods, oligomeric or small-molecule library compounds capable of interacting specifically with a selected biological agent, such as a biomolecule, a macromolecule complex, or cell, are screened utilising a combinational library device which is easily chosen by the person of skill in the art from the range of well-known methods, such as those described above. In such a method, each member of the library is screened for its ability to interact specifically with the selected agent. In practising the method, a biological agent is drawn into compound-containing tubes and allowed to interact with the individual library compound in each tube. The interaction is designed to produce a detectable signal that can be used to monitor the presence of the desired interaction. Preferably, the biological agent is present in an aqueous solution and further conditions are adapted depending on the desired interaction. Detection may be performed for example by any well-known functional or non-functional based method for the detection of substances.

In addition to screening for molecules which mimic the activity of LM04, it may also be desirable to identify and utilise molecules which function agonistically or antagonistically in order to up or down-regulate the functional activity of the LM04. The use of such molecules is described in more detail below. To the extent that the subject molecule is proteinaceous, it may be derived, for example, from natural or recombinant sources including fusion proteins or following, for example, the screening methods described above. The non-proteinaceous molecule may be, for example, a chemical or synthetic molecule which has also been identified or generated in accordance with the methodology identified above. Accordingly, the present invention contemplates the use of chemical analogues capable of acting as agonists or antagonists. Chemical agonists may not necessarily be derived from LM04 but may share certain conformational similarities. Alternatively, chemical agonists may be specifically designed to mimic certain physiochemical properties of LM04.

Screening for the modulatory agents hereinbefore defined can be achieved by any one of several suitable methods including, but in no way limited to, contacting a cell comprising LM04 with an agent and screening for the modulation of LM04-related functional activity or modulation of the activity or expression of a downstream LM04 cellular target. Detecting such modulation can be achieved utilising techniques such as Western blotting, electrophoretic mobility shift assays and/or the readout of reporters of sphingosine kinase or TRAF activity such as luciferases, CAT and the like.

It should be understood that the LM04 protein may be naturally occurring in the cell which is the subject of testing or the gene encoding it may have been transfected into a host cell for the purpose of testing. Further, the naturally occurring or transfected gene may be constitutively expressed—thereby providing a model useful for, inter alia, screening for agents which down-regulate LM04 expression or activity or the gene may require activation—thereby providing a model useful for, inter alia, screening for agents which modulate LM04 expression or activity under certain stimulatory conditions. Further, to the extent that a LM04 nucleic acid molecule is transfected into a cell, that molecule may comprise the entire LM04 gene or it may merely comprise a portion of the gene such as the LM04 binding portion.

In another example, the subject of detection could be a downstream LM04 regulatory target, rather than LM04 itself, such as CtIP or BRCA1. Yet another example includes LM04 binding sites ligated to a minimal reporter. This is an example of a system where modulation of the molecules which LM04 regulates the activity of, are monitored. Where the cell which is the subject of the screening system is a neoplastic cell, for example, modulation of LM04 expression or activity could be detected by screening for the modulation of cellular proliferation.

Accordingly, another aspect of the present invention provides a method for detecting an agent capable of modulating LM04 expression or LM04 functional activity said method comprising contacting a cell or extract thereof containing said LM04 or LM04 with a putative agent and detecting an altered expression phenotype associated with said interaction.

Reference to detecting an "altered expression phenotype associated with said interaction" should be understood as the detection of cellular changes associated with modulation of LM04 expression or LM04 activity. These may be detectable, for example, as intracellular changes or changes observable extracellularly. For example, this includes, but is not limited to, detecting changes in downstream product levels or activities.

In a related aspect, the present invention should be understood to extend to the agents identified utilising any of the methods hereinbefore defined. In this regard, reference to an agent should be understood as a reference to any proteinaceous or non-proteinaceous molecule which modulates at least one LM04-related functional activity.

Said proteinaceous or non-proteinaceous molecule may act either directly or indirectly to modulate LM04 expression or LM04 activity. Said molecule acts directly if it associates with LM04 molecules Said molecule acts indirectly if it associates with a molecule other than LM04, which other molecule either directly or indirectly modulates the expression or activity of LM04. Accordingly, the method of the present invention encompasses regulation of LM04 expression or activity via the induction of a cascade of regulatory steps.

Although the preferred method is to down-regulate LM04 expression or LM04 functional activity, it should be understood that there may be situations in which it is desirable to up-regulate proliferation, in a controlled manner for example, by up-regulating LM04 expression or LM04 functional activity. Accordingly, the method of the present invention should be understood to extend to such applications.

It should be understood that the cell which is treated according to the method of the present invention may be located ex vivo or in vivo. By "ex vivo" is meant that the cell has been removed from the body of a subject wherein the modulation of its proliferation will be initiated in vitro. For example, the cell may be a non-neoplastic cell which is to undergo long term culture and is therefore stimulated to undergo ongoing LM04 induced proliferation, which proliferation is up-regulated by agonists of LM04 activity. In accordance with the preferred aspects of the present invention, the cell may be a neoplastic cell, such as a malignant cell, located in vivo (such as in the breast) and the down-regulation of its growth will be achieved by applying the method of the present invention in vivo to down-regulate the level of LM04.

A further aspect of the present invention relates to the use of the invention in relation to the treatment and/or prophylaxis of disease conditions. Without limiting the present invention to any one theory or mode of action, LM04 has been shown to regulate mammary cell proliferation. Accordingly, the method of the present invention provides a valuable tool for modulating aberrant or otherwise unwanted LM04-regulated proliferative activity.

Accordingly, another aspect of the present invention is directed to the method for the treatment and/or prophylaxis of a conditions characterised by aberrant, unwanted or otherwise inappropriate LM04-regulated proliferative activity in a mammal, said method comprising administering to said mammal an effective amount of an agent for a time and under conditions sufficient to modulate LM04 expression or LM04 functional activity wherein inhibiting or otherwise antagonising said expression or activity down-regulates said cellular proliferation.

Reference to "aberrant, unwanted or otherwise inappropriate" cellular proliferation should be understood as a reference to overactive cellular proliferation, to physiologically normal cellular proliferation which is inappropriate in that it is unwanted or to insufficient cellular proliferation. For example, LM04 expression in mammary cells is thought to lead to deregulation of differentiation and subsequently to uncontrolled breast cell proliferation.

Accordingly, in one preferred embodiment there is provided a method for the treatment and/or prophylaxis of a neoplastic condition said method comprising administering to said mammal an effective amount of an agent for a time and under conditions sufficient to down-regulate LM04 expression or LM04 functional activity wherein inhibiting or otherwise antagonising said expression or activity down-regulates cellular proliferation.

Preferably, said neoplastic condition is breast cancer.

The term "mammal" as used herein includes humans, primates, livestock animals (eg.

sheep, pigs, cattle, horses, donkeys), laboratory test animals (eg. mice, rabbits, rats, guinea pigs), companion animals (eg. dogs, cats) and captive wild animals (eg. foxes, kangaroos, deer). Preferably, the mammal is human or a laboratory test animal Even more preferably, the mammal is a human.

An "effective amount" means an amount necessary at least partly to attain the desired response, or to delay the onset or inhibit progression or halt altogether, the onset or progression of a particular condition being treated. The amount varies depending upon the health and physical condition of the individual to be treated, the taxonomic group of individual to be treated, the degree of protection desired, the formulation of the composition, the assessment of the medical situation, and other relevant factors. It is expected that the amount will fall in a relatively broad range that can be determined through routine trials.

Reference herein to "treatment" and "prophylaxis" is to be considered in its broadest context. The term "treatment" does not necessarily imply that a subject is treated until total recovery. Similarly, "prophylaxis" does not necessarily mean that the subject will not eventually contract a disease condition. Accordingly, treatment and prophylaxis include amelioration of the symptoms of a particular condition or preventing or otherwise reducing the risk of developing a particular condition. The term "prophylaxis" may be considered as reducing the severity or onset of a particular condition. "Treatment" may also reduce the severity of an existing condition.

The present invention further contemplates a combination of therapies, such as the administration of the agent together with subjection of the mammal to circulating cytotoxic agents or to radiotherapy in the treatment of cancer.

Administration of the modulatory agent, in the form of a pharmaceutical composition, may be performed by any convenient means. The modulatory agent of the pharmaceutical composition is contemplated to exhibit therapeutic activity when administered in an amount which depends on the particular case. The variation depends, for example, on the human or animal and the modulatory agent chosen. A broad range of doses may be applicable. Considering a patient, for example, from about 0.1 mg to about 1 mg of modulatory agent may be administered per kilogram of body weight per day. Dosage regimes may be adjusted to provide the optimum therapeutic response. For example, several divided doses may be administered daily, weekly, monthly or other suitable time intervals or the dose may be proportionally reduced as indicated by the exigencies of the situation.

The modulatory agent may be administered in a convenient manner such as by the oral, intravenous (where water soluble), intraperitoneal, intramuscular, subcutaneous, intradermal or suppository routes or implanting (e.g. using slow release molecules). The modulatory agent may be administered in the form of pharmaceutically acceptable nontoxic salts, such as acid addition salts or metal complexes, e.g. with zinc, iron or the like (which are considered as salts for purposes of this application). Illustrative of such acid addition salts are hydrochloride, hydrobromide, sulphate, phosphate, maleate, acetate, citrate, benzoate, succinate, malate, ascorbate, tartrate and the like. If the active ingredient is to be administered in tablet form, the tablet may contain a binder such as tragacanth, corn starch or gelatin; a disintegrating agent, such as alginic acid; and a lubricant, such as magnesium stearate.

Routes of administration include, but are not limited to, respiratorally, intratracheally, nasopharyngeally, intravenously, intraperitoneally, subcutaneously, intracranially, intradermally, intramuscularly, intraoccularly, intrathecally, intracereberally, intranasally, infusion, orally, rectally, via IV drip patch and implant.

In accordance with these methods, the agent defined in accordance with the present invention may be coadministered with one or more other compounds or molecules. By "coadministered" is meant simultaneous administration in the same formulation or in two different formulations via the same or different routes or sequential administration by the same or different routes. For example, the subject agent may be administered together with an agonistic agent in order to enhance its effects. By "sequential" administration is meant a time difference of from seconds, minutes, hours or days between the administration of the two types of molecules. These molecules may be administered in any order.

Another aspect of the present invention contemplates the use of an agent, as hereinbefore defined, in the manufacture of medicament for the treatment of a condition in a mammal, which condition is characterised by aberrant, unwanted or otherwise inappropriate LM04-regulated cellular proliferation, wherein said agent modulates LM04 expression or LM04 activity and wherein inhibiting or otherwise antagonising said expression or activity down-regulates said cellular proliferation.

In yet another further aspect, the present invention contemplates a pharmaceutical composition comprising the modulatory agent as hereinbefore defined together with one or more pharmaceutically acceptable carriers and/or diluents. Said agents are referred to as the active ingredients.

The pharmaceutical forms suitable for injectable use include sterile aqueous solutions (where water soluble) or dispersions and sterile powders for the extemporaneous preparation of sterile injectable solutions or dispersion or may be in the form of a cream or other form suitable for topical application. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of superfactants. The preventions of the action of microorganisms can be brought about by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilisation. Generally, dispersions are prepared by incorporating the various sterilised active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When the active ingredients are suitably protected they may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like.

Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions in such that a suitable dosage will be obtained. Preferred compositions or preparations according to the present invention are prepared so that an oral dosage unit form contains between about 0.1 µg and 2000 mg of active compound.

The tablets, troches, pills, capsules and the like may also contain the components as listed hereafter: a binder such as gum, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound(s) may be incorporated into sustained-release preparations and formulations.

The pharmaceutical composition may also comprise genetic molecules such as a vector capable of transfecting target cells where the vector carries a nucleic acid molecule encoding a modulatory agent. The vector may, for example, be a viral vector.

Yet another aspect of the present invention relates to the agent as hereinbefore defined, when used in the method of the present invention.

The present invention is further defined by the following non-limiting examples:

EXAMPLE 1

The LIM Domain Protein LM04 Inhibits Differentiation of Mammary Epithelial Cells In Vitro and is Overexpressed in Breast Cancer Materials and Methods Cell Lines Most of the cell lines have been cited in previous studies (Douglas, A. M., Grant, S. L., Goss, G. A., Clouston, D. R., Sutherland, R. L. & Begley, C. G. (1998) *Int J Cancer* 75, 64-73). SCp2 mammary epithelial cells (Desprez, P.-Y., Roskelley, C., Campisi, J. & Bissell, M. J. (1993) *Mol. Cell. Diff.* 1, 99-110) were kindly provided by Dr M. Bissell.

In Situ Hybridisation

Mouse Lmo4 was isolated from mouse T cells by affinity chromatography using rabbit anti-Ldb1 antisera (19). The purification and cloning of Lmo4 will be described elsewhere (K. H.). Full-length human LMO4 (from ATCC, Acc. No. T09407) or mouse Lmo4 cDNAs were cloned into Bluescript SKII (Stratagene). Antisense and sense riboprobes were generated using T3 or T7 RNA polymerase (Promega) with digoxigenin-UTP (Roche). Standard in situ hybridisations were performed as described (Wilkinson, D. (1992) In Situ Hybridisation (IRL, New York)). Breast cancer tissue arrays were either purchased from Clinomics or prepared from breast cancer samples at the Peter MacCallum Cancer Institute (PMCI), Melbourne, Australia. All specimens evaluated were anonymous, archival tissue specimens. The Peter MacCallum Institutional Review Board approved the use of PMCI specimens for tissue array analysis.

SCp2 Cell Differentiation Assay

SCp2 mammary epithelial cells (Desprez, P.-Y., Roskelley, C., Campisi, J. & Bissell, M. J. (1993) *Mol. Cell. Diff.* 1:99-110) were passaged in DMEM-F12 media containing DMEM-HAM, 10% FCS, and insulin 5 µg/ml (Sigma). Full-length mouse cDNAs corresponding to Lmo4 or Ldb1 were cloned into both the pEF1α-puro and pEF1α-Flag-puro mammalian expression vectors (Huang, D. C., Cory, S. & Strasser, A. (1997) *Oncogene* 14, 405-14). Protein expression was confirmed by transient transfection of 293T cells. Linearized expression vectors (10 µg) were introduced into SCp2 cells using Superfect (Qiagen) and selected in puromycin for 8-10 days. Pools of stable transfectants expressing the appropriate gene or vector alone (control) were then used in the differentiation assay, essentially as described (Desprez, P.-Y., Roskelley, C., Campisi, J. & Bissell, M. J. (1993) *Mol. Cell. Diff.* 1:99-110). Transfectants were induced to differentiate by the addition of DMEM-F12 containing insulin (5 µg/ml), hydrocortisone (1 µg/ml) and prolactin (5 µg/ml), which was generously provided by Dr A. Parlow (National Hormone and Pituitary Program). After 96 hours, cells were harvested directly for RNA extraction.

RNA Analysis and RT-PCR

Northern analysis of poly(A)$^+$ RNA was performed as described (Visvader, J., Begley, C. G. & Adams, J. M. (1991) *Oncogene* 6, 187-94). Total RNA was isolated from SCp2 cells on ECM using RNAzol (Tel-Test); cDNA synthesis and PCR were performed as described (Weiss, M. J., Keller, G. & Orkin, S. H. (1994) *Genes Dev* 8, 1184-97), using primers for β-casein, Wap and Hprt (Weiss, M. J., Keller, G. & Orkin, S. H. (1994) *Genes Dev* 8, 1184-97). Sequences of the β-casein primers were: forward 5'-ATGAAGGTCTTCATCCTCGC-CTGCC-3' (SEQ ID NO:1) and reverse 5'-GCTGGACCA-GAGACTGAGGAAGGTGC-3' (SEQ ID NO:2). Sequences of the Wap primers were: forward 5'-TAGCAGCAGAT-TGAAAGCATTATG-3' (SEQ ID NO:3) and reverse 5'-GA-CACCGGTACCATGCGTTG-3' (SEQ ID NO:4). Samples were fractionated on agarose gels, ethidium bromide stained, blotted, then hybridised with specific internal oligonucleotides.

Immunoprecipitation and Western Analysis

Whole cell lysates were generated from stably transfected SCp2 pools by lysing cells in KALB lysis buffer (Nicholson, S. E., Willson, T. A., Farley, A., Starr, R., Zhang, J. G., Baca, M., Alexander, W. S., Metcalf, D., Hilton, D. J. & Nicola, N. A. (1999) *EMBO J* 18, 375-85) containing protease inhibitors. Proteins were immunoprecipitated with anti-Flag M2 (Sigma) and protein G Sepharose (Pharmacia), and separated by SDS-PAGE (Novex). After transfer, filters were blocked and incubated with rabbit antisera to either full-length mouse Lmo4 or a C-terminal Ldb1 polypeptide (19). Antibody binding was visualised with peroxidase-conjugated anti-mouse antibody by ECL (Amersham).

Immunohistochemistry

For immunostaining, tissue arrays (Clinomics) were incubated with supernatant containing rat anti-LMO4 monoclonal antibody, followed by incubation with biotinylated anti-rat IgG and HRP-Streptavidin (Dako), before detection using DAB (Dako), as described (Armes, J. E., Trute, L., White, D., Southey, M. C., Hammet, F., Tesoriero, A., Hutchins, A. M., Dite, G. S., McCredie, M. R., Giles, G. G., Hopper, J. L. & Venter, D. J. (1999) *Cancer Res* 59, 2011-7). Generation of the LMO4 monoclonal antibody will be described elsewhere. Other primary monoclonal antibodies used were: anti-ERα (1D5), anti-PgR (636) and anti-ErbB2 (all from Dako).

EXAMPLE 2

LM04 is Developmentally Regulated in the Mouse Mammary Gland

In situ hybridisation analysis revealed that Lmo4 was prominently expressed in the lobuloalveolar units of the mammary gland during pregnancy (FIG. 1A). At this stage, there is a high rate of proliferation accompanying the formation and expansion of the lobuloalveoli. Lower levels of Lmo4 mRNA were present in the ductal epithelium of the virgin mammary gland, evident as a single layer, and in the early lactating and involuting mammary glands. Staining of the surrounding stroma was also apparent in the virgin mammary gland. The high level of Lmo4 in the pregnant mammary gland (FIG. 1A) was confirmed by Northern analysis, which revealed that levels of the two major transcripts (approximately 1.8 and 2.3 kb) peaked at mid-pregnancy (day 12) and remained high until late pregnancy (FIG. 1B). Interestingly, although Lmo4 expression decreased during lactation, it appeared to be upregulated during involution.

EXAMPLE 3

Figure 3:
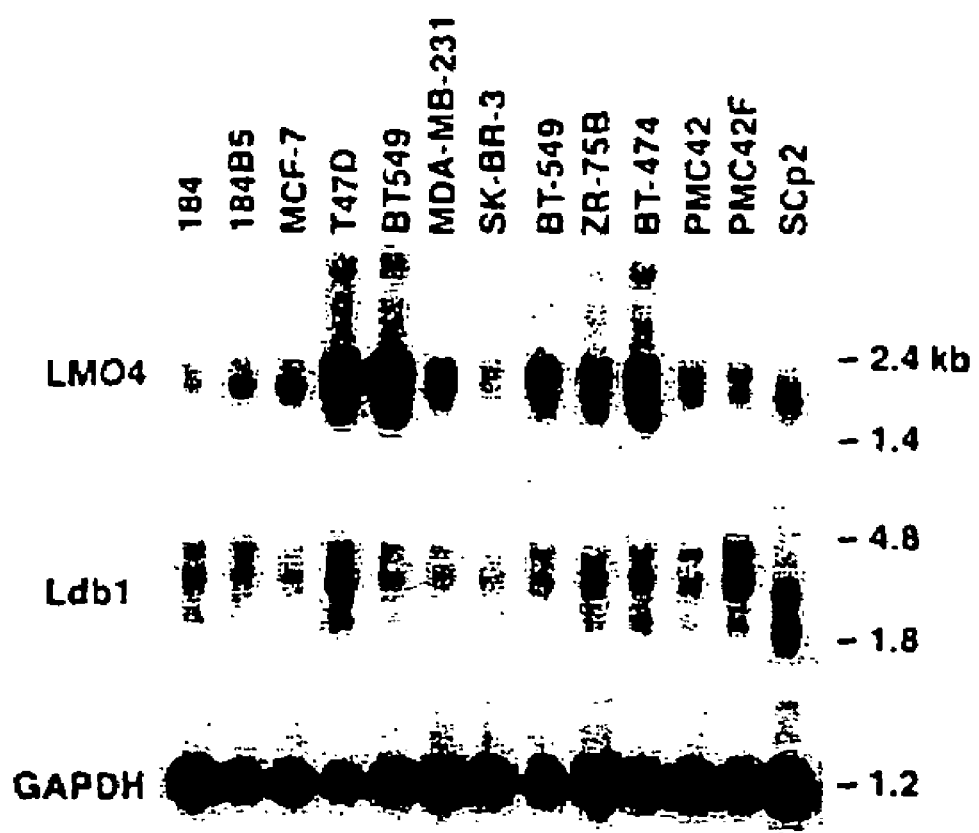
FIG. 3: LMO4 is overexpressed in several human breast cancer cell lines. Northern analysis of poly(A)$^+$ RNA (3 μg) from human and mouse (SCp2) breast epithelial cell lines. Filters were sequentially hybridised with mouse Lmo4, Ldb1 and Gapdh cDNA probes. The lower molecular weight LDB1 transcript in human breast cancer cell lines may represent a cross-hybridising species. Sizes of the Lmo4 and Ldb1 transcripts were lower in the mouse SCp2 cell line relative to those in human cell lines.

Forced Expression of the LM04 and LDB1 Genes Inhibits β-Casein Synthesis in Mammary Epithelial Cells Lmo4 binds with high affinity to Ldb1, a nuclear protein that serves as an adaptor for several LIM domain-containing proteins. To examine the role of Lmo4 and its partner protein Ldb1 in mammary differentiation, we introduced the genes into SCp2 mammary epithelial cells, which express moderate levels of Lmo4 and Ldb1 RNA (FIG. 3). The SCp2 cell line was originally isolated from the mammary gland of a mid-gestation mouse and mimics the essential features of mammary differentiation in the presence of extracellular matrix (ECM) and a lactogenic stimulus (Desprez, P.-Y., Roskelley, C., Campisi, J. & Bissell, M. J. (1993) *Mol. Cell. Diff.* 1, 99-110). Differentiation of SCp2 cells is accompanied by the production of milk proteins, such as β-casein and whey acidic protein (Wap), which we have used here as molecular markers. Stable transfectants of SCp2 cells harboring Lmo4 or Ldb1 cDNAs (either epitope-tagged or untagged) together with a puromycin resistance marker, were generated and pools of cells assayed for their ability to undergo differentiation. For the latter assay, transfectants were plated on ECM in the presence or absence of a lactogenic stimulus (prolactin, insulin and hydrocortisone).

Figure 2:
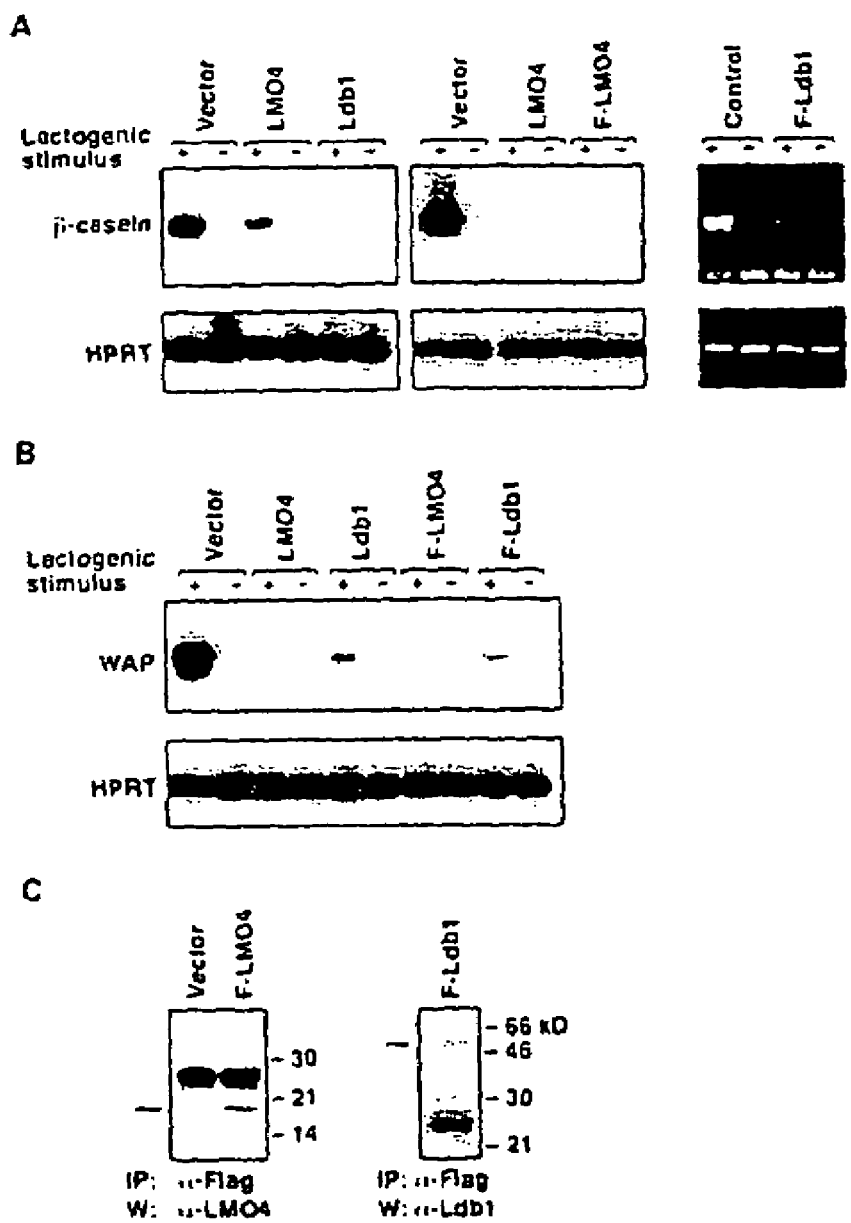
FIG. 2: Lmo4 and Ldb1 inhibit β-casein and whey acidic protein (Wap) RNA synthesis in SCp2 mammary cells induced to differentiate. (A) RT-PCR analysis was performed using total RNA derived from stably transfected SCp2 pools that were stimulated (+) with prolactin, insulin and hydrocortisone or unstimulated (−) for 96 hrs. β-casein and Hprt were used as markers of differentiation and loading, respectively. At least five independent transfections were performed. PCR products were fractionated by gel electrophoresis, blotted and hybridised with internal oligonucleotide probes. The ethidium bromide stained gel for Flag-Ldb1 is shown in rightmost-panel. (B) RT-PCR analysis was performed on the same pools of transfectants as shown in (A), using primers specific for Wap and Hprt. (C) Immunoprecipitation and Western blot analysis confirmed expression of Flag-Lmo4 and Flag-Ldb1 in SCp2 transfectants. Lysates from cells expressing either gene or containing empty vector were subjected to immunoprecipitation using mouse anti-Flag antibody and then blotted with rabbit anti-Lmo4 or rabbit anti-Ldb1 antibody. Arrows indicate relevant proteins.

Overexpression of Lmo4 or Ldb1 markedly inhibited mRNA expression of β-casein and Wap upon treatment with a lactogenic stimulus. In contrast, transfectants expressing empty vector were indistinguishable from parental cells (FIGS. 2A and B). Expression of the Flag-tagged Lmo4 and Ldb1 proteins was readily detectable in several SCp2 transfectants, examples of which are shown in FIG. 2C, while expression of the untagged transgenes was verified by Northern analysis (data not shown). Forced expression of antisense Lmo4 RNA in SCp2 and HCl1 mammary epithelial cells consistently augmented β-casein synthesis by several-fold, although Lmo4 protein levels were only slightly reduced by western analysis (data not shown). Taken together, the data indicate that Lmo4 and its partner protein Ldb1 play a role in maintaining proliferation rather than differentiation of mammary epithelial cells.

EXAMPLE 4

Overexpression of LM04 in Breast Cancer Cell Lines and Primary Invasive Cancers LM04 RNA levels vary markedly between different human breast epithelial cancer cell lines (FIG. 3). High levels of LMO4 mRNA were detected in five out of ten breast cancer cell lines. Interestingly, transcript levels were low in the immortalised cell line 184 but were substantially higher in a transformed variant of this line, 184B5 (Douglas, A. M., Grant, S. L., Goss, G. A., Clouston, D. R., Sutherland, R. L. & Begley, C. G. (1998) *Int J Cancer* 75, 64-73). LDB1 was expressed as two major transcripts (2.3 and 3.5 kb) amongst the panel of breast cancer cell lines and showed less variation in the extent of expression. The size of the Lmo4 and Ldb1 transcripts in SCp2 (FIG. 3), HCl1 and EpH4 (not shown) mouse mammary epithelial cells was lower than that of the corresponding human RNAs, and reflects a species difference.

Figure 4:
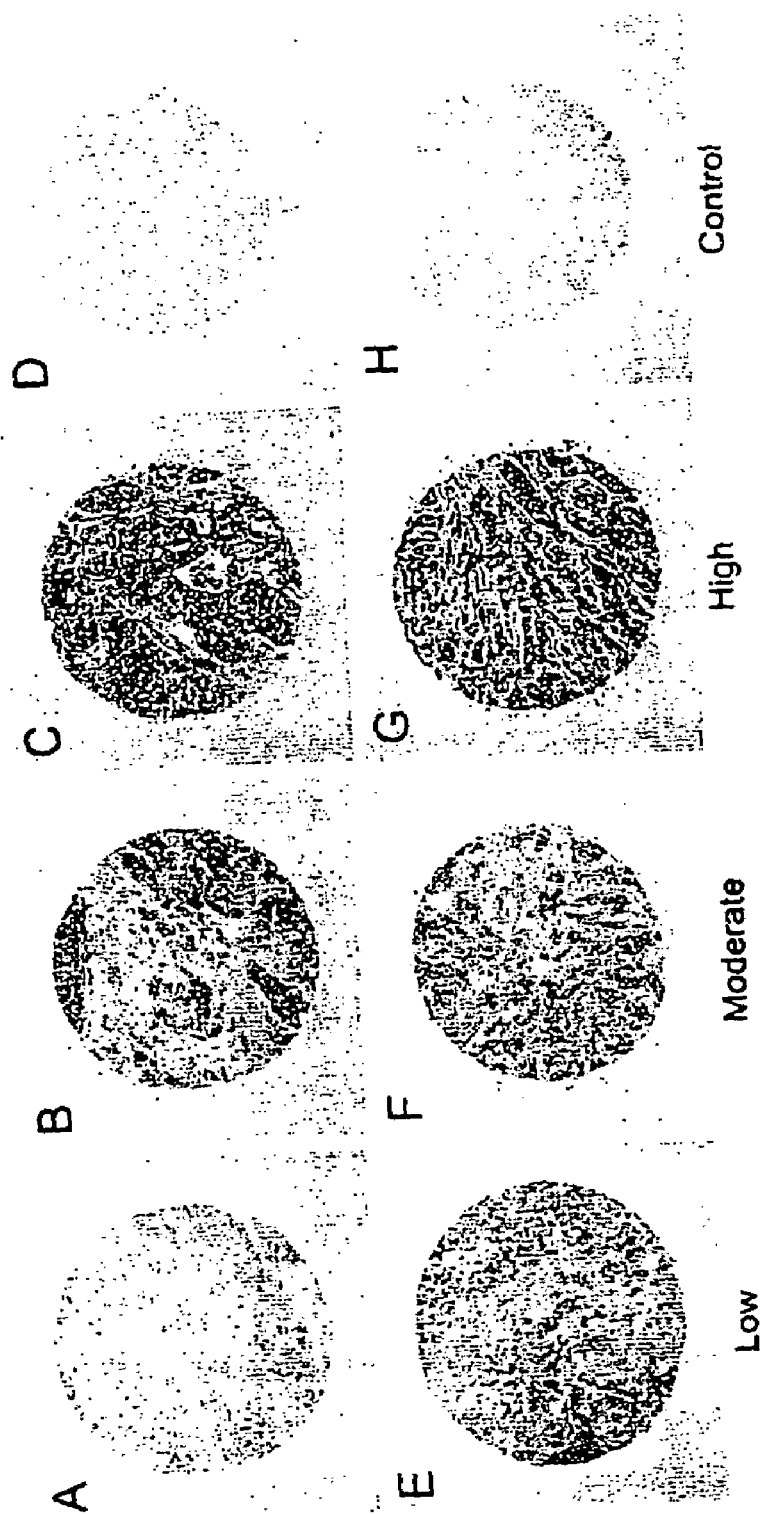
FIG. 4: Overexpression of LMO4 RNA in primary breast cancer. In situ hybridisation using full-length human LMO4 sense and antisense riboprobes labeled with digoxigenin. Low magnification of tumor specimens displaying low (A and E), moderate (B and F) and high (C and G) levels of LMO4 mRNA. The LMO4 sense riboprobe gave negligible staining (D and H). Sense controls (D and H) correspond to the tumors shown in C and G, respectively.
Figure 5:
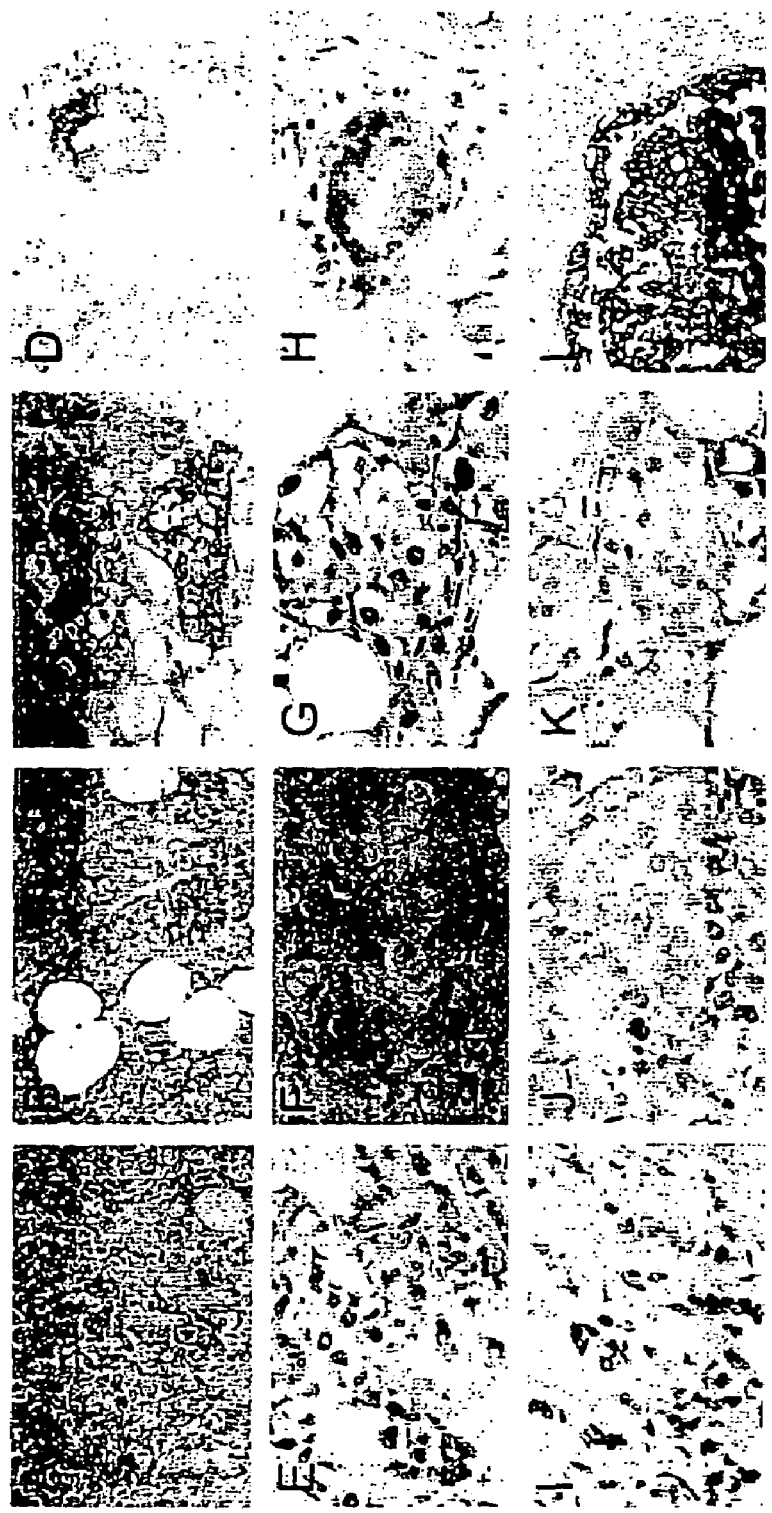
FIG. 5: Overexpression of LMO4 RNA and LMO4 protein in primary breast cancer. In situ hybridisation (using digoxigenin-labeled human LMO4 riboprobes) and immunohistochemistry (using a rat anti-LMO4 monoclonal antibody) were performed on tissue arrays containing archival breast specimens. High LMO4 RNA expression in an infiltrating lobular carcinoma (A), and two infiltrating ductal carcinomas (B and C) (antisense LMO4 probe); (D) Benign fibroadenoma, displaying low expression of LMO4. Abundant LMO4 protein expression was detected in the corresponding infiltrating lobular and ductal cancer samples (E, F and G). Low levels of LMO4 protein were detected in the benign sample (H). Corresponding negative controls (Ig) for immunostaining are shown (I, J and K); (L) Ductal carcinoma in situ (DCIS), showing high expression of LMO4 RNA. Sense LMO4 probe gave no signal for any of the tumor samples. Orig. mag. A-D, 100×; E-K, 200×; L, 50×.

To assess whether LMO4 was upregulated in primary breast cancers, we performed in situ hybridisation on tissue arrays comprising 177 invasive breast cancers. Tumor specimens were scored as low/negative, moderate or high for expression of LMO4 based on their intensity of hybridisation to the human LMO4 riboprobe. Two examples within each intensity group are given in FIG. 4 at low magnification. The control sense probe gave a negligible signal (FIG. 4D, H). Strong to moderate staining of LMO4 RNA was evident in 99 of 177 (56%) cancers, most of which corresponded to infiltrating ductal carcinomas but also included invasive lobular and mixed ductal and lobular carcinomas. FIG. 5 depicts prominent expression of LMO4 in an invasive lobular carcinoma (FIG. 5A) and two infiltrating ductal carcinomas (FIGS. 5B, C). Low levels were detected in 7 out of 20 (35%) benign breast fibroadenomas (FIG. 5D) or normal breast tissue samples. LMO4 RNA levels appeared to be elevated in ductal carcinoma in situ (DCIS) (FIG. 5L), in which 7 of 18 (38%) pre-invasive tumors showed strong to moderate staining. A subset comprising 60 tumors was also analysed by immunohistochemistry using a rat anti-LMO4 monoclonal antibody. Overexpression of LMO4 protein was observed in 62% of tumors. A comparison of in situ RNA and immunohistochemical staining for three tumors is shown in FIGS. 5(A and E, B and F, C and G, respectively), revealing overexpression of LMO4 at both the RNA and protein levels. Benign breast tissue displayed either low (FIG. 5H) or undetectable levels of LMO4 protein. Anti-immunoglobulin antibody controls gave negligible staining for all tumor samples (FIGS. 5I, J and K). In this subset of 60 tumors, 35 (58%) scored high for RNA expression. Of these, 25 tumors (71%) also expressed high levels of LMO4 protein while 10 tumors displayed lower levels of protein. Conversely, 11 (17%) of 60 tumors that gave weak staining for LMO4 RNA, scored high for protein expression. In summary, there was a strong correlation between RNA and protein overexpression in 71% of cases. The discordance observed for a minority of tumors is likely to reflect the numerous mechanisms that regulate the stability and turnover of RNA and protein, as well as the integrity of the primary cancer tissues collected by biopsy. For example, deregulation of a Cyclin D1 protein degradation pathway has been reported in breast cancer, such that Cyclin D1 proteins levels are high despite low RNA expression (Russell, A., Thompson, M. A., Hendley, J., Trute, L., Armes, J. & Germain, D. (1999) *Oncogene* 18, 1983-91).

Subcellular localisation of LMO4 was found to be variable. In some tumors, prominent nuclear staining was detected (FIGS. 5E and G) whereas in other tumors, nuclear plus cytoplasmic staining was visualised (FIG. 5F). These findings are consistent with subcellular localisation studies of LMO4 in transfected cells (Kenny, D. A., Jurata, L. W., Saga, Y. & Gill, G. N. (1998) *Proc Natl Acad Sci USA* 95, 11257-62, Sugihara, T. M., Bach, I., Kioussi, C., Rosenfeld, M. G. & Andersen, B. (1998) *Proc Natl Acad Sci USA* 95, 15418-23). The same tumor set of 60 samples was evaluated for expression of the Estrogen (ERα), Progesterone and ErbB2 receptors by immunohistochemistry, in which 32%, 40% and 30% were positive for the respective receptors. No correlation was found between overexpression of LMO4 and expression of these markers.

EXAMPLE 5

The LIM Domain Protein LMO4 Interacts with the Corepressor CtIP and the Tumor Suppressor BRCA1 and Inhibits BRCA1 Activity Materials and Methods Plasmids The pGBT9-LMO4 bait plasmid was generated by PCR amplification of mouse LMO4 in pSP72 using the following primers: forward 5'-CGCGGATCCCCGGCTCCCTCTC-CTGGAAGCGCTGC-3' (SEQ ID NO:5) and reverse 5'-CGCGGATCCTCAGCAGACCTTCTGGTCTGCCAG-3' (SEQ ID NO:6); the resultant product was inserted into the BamHI site of pGBT9 (Clontech). The first LIM domain (residues 1-82) of LMO4 was PCR amplified using the forward primer 5'-CGCGGATCCTGAATCCGGGCAG-CAGCTCGC-3' (SEQ ID NO:7) and the reverse primer 5'-CGCGGATCCTCACCCAAATAACCTAATG-TAGTCATT-3' (SEQ ID NO:8), then cloned into the BamH1 site of the Flag-pEF1α-puro vector (Huang, D. C., Cory, S., and Strasser, A. (1997) *Oncogene* 14(4), 405-14). The second LIM domain (residues 79-165) of LMO4 was PCR amplified using the forward primer 5'-CGCGGATCCGGTTATTTGG-GAATAGCGGTGCTTG-3' (SEQ ID NO:9) and the reverse primer 5'-CGCGGATCCTCAGCAGACCTTCTGGTCT-GCCAG-3' (SEQ ID NO: 10), and subsequently cloned into the BamH1 site of the Flag-pEF1α-puro vector. Expression vectors encoding Lhx1 or Lhx3 (pSV-sport-Flag) and LMK1 were kindly provided by A. Agulnick and O. Bernard, respectively. Full-length cDNAs corresponding to the coding region of mouse or human LMO4 were cloned into the Flag-pEF1α-puro expression vector, and a 0.7 kb mouse LMO4 cDNA fragment was cloned into pEF1α-puro vector. The expression plasmids encoding residues 45-897 of human CtIP (pCMV-HA-ns311), human BRCA1 (pcDNA3-HA-BRCA1) and mouse LMO2 (pEF1αx-Flag-LMO2) have previously been described (Visvader, J. E., Mao, X., Fujiwara, Y., Hahm, K., and Orkin, S. H. (1997) *Proc Natl Acad Sci USA* 94(25), 13707-12; 19;Scully, R., Chen, J., Plug, A., Xiao, Y., Weaver, D., Feunteun, J., Ashley, T., and Livingston, D. M. (1997) *Cell* 88(2), 265-75). HA-tagged CtIP deletion mutants were generated either by PCR amplification or subcloning from plasmids (Yu, X., Wu, L. C., Bowcock, A. M., Aronheim, A., and Baer, R. (1998) *J Biol Chem* 273(39), 25388-92), into the expression vectors HA-pcDNA3.1 or HA-EF1α-puro. The SZ fragment of BRCA1 (residues 1528-1863) was recloned from pCMV-Gal4b-BR-SZ (Yu, X., Wu, L. C., Bowcock, A. M., Aronheim, A., and Baer, R. (1998) *J Biol Chem* 273(39), 25388-92) into HA-pcDNA3.1. Myc-tagged derivatives of wild-type and mutant BRCA1 were cloned into pcDNA3.0 (J. C., unpub.).

The yeast expression construct encoding the activation domain (AD) of BRCA1 fused to the Gal4 DNA-binding domain (DBD) was generated by PCR amplification of the region spanning amino acids 1293-1863 of BRCA1 and subsequent cloning into pGBT9 (Clontech). The mammalian Gal4DBD-AD fusion construct was generated by cloning a cDNA fragment encoding the BRCA1-AD region into pCMV-Gal4b (Yu, X., Wu, L. C., Bowcock, A. M., Aronheim, A., and Baer, R. (1998) *J Biol Chem* 273(39), 25388-92). Full-length cDNA encoding mouse LMO4 was inserted into the yeast expression plasmid pYX212 (Ingenious). The reporter plasmid, pG5CAT, was from Clontech. Details of plasmid constructions are available on request.

Yeast Two-Hybrid Screen

The pGBT9-LMO4 bait plasmid (residues 15-165) was used to screen $8.4 \times 10^6$ transformants from a primary breast adenocarcinoma cDNA library (Byrne, J. A., Nourse, C. R., Basset, P., and Gunning, P. (1998) *Oncogene* 16(7), 873-81), following standard protocols (Clontech Matchmaker Two-Hybrid System).

Antibody Production

Full-length mouse LMO4 cDNA was amplified by PCR and subcloned into pGEX-2T (Amersham Pharmacia Biotech.). The GST-LMO4 fusion protein was expressed in the bacterial strain UT5600, purified according to standard protocols (Smith, D. B., and Johnson, K. S. (1988) *Gene* 67(1), 31-40) and used to inject rabbits to produce polyclonal antisera. The generation of rat LMO4-specific monoclonal antibodies will be described elsewhere.

Immunoprecipitation and Western Blot Analysis

Human embryonal kidney 293T cells (10 cm plates) were transiently transfected with 4 μg of each expression construct and/or empty vector using the calcium phosphate precipitation method. Cell extracts (0.5 ml) were prepared in whole cell lysis buffer (150 mM NaCl, 5 mM EDTA, 50 mM Tris pH7.5, 1% Nonidet P-40, 1 mM DTT) containing protease inhibitors (1 mM phenylmethylsulfonyl fluoride, 1 μg/ml leupeptin, 1 μg/ml pepstatin, 1 μg/ml aprotinin) and normalised for protein concentration, as determined by Bradford analysis (BioRad). Proteins were immunoprecipitated with either anti-Flag M2 (Sigma) or anti-myc 9E10 and protein G sepharose (Amersham Pharmacia Biotech.), and separated by SDS-PAGE (Novex). After transfer to PVDF membranes (Millipore), filters were blocked and incubated with rabbit antisera against CtIP or Ldb1 (Visvader, J. E., Mao, X., Fujiwara, Y., Hahm, K., and Orkin, S. H. (1997) *Proc Natl Acad Sci USA* 94(25), 13707-12) or mouse anti-BRCA1 monoclonal antibody MS110 (Oncogene Research Products). Filters were then incubated with HRP-coupled secondary antibodies, and developed by ECL (Amersham Pharmacia Biotech.).

For detection of endogenous proteins, nuclear extracts from human HBL100 cells were prepared (Watters, D., Khanna, K. K., Beamish, H., Birrell, G., Spring, K., Kedar, P., Gatei, M., Stenzel, D., Hobson, K., Kozlov, S., Zhang, N., Farrell, A., Ramsay, J., Gatti, R., and Lavin, M. (1997) *Oncogene* 14(16), 1911-21). Proteins were immunoprecipitated with either anti-LMO4 rabbit antisera or a rat anti-LMO4 monoclonal antibody and protein G sepharose, and fractionated by SDS-PAGE. After transfer, filters were blocked and incubated with mouse monoclonal antibodies to either CtIP (14.1) (Yu, X., and Baer, R. (2000) *J Biol Chem* 275(24), 18541-9) or BRCA1 (MS110, Oncogene Research Products), followed by incubation with HRP-coupled secondary antibodies, and developed by ECL (Amersham Pharmacia Biotech.).

In Vitro Binding Assay

In vitro synthesis of $^{31}$S-labelled BRCA1 (C-terminal residues 1528-1863) was performed by in vitro transcription/translation of HA-pCDNA3.1-BRCA1-SZ using the TNT T7 coupled reticulocyte lysate system (Promega). Binding assays were carried out with a 10 µl aliquot of $^{31}$S-labeled BRCA1-SZ primed lysate and 100 µl (50% slurry of GST-sepharose beads; Amersham Pharmacia) of GST-LMO4 or GST-only protein in GST interaction buffer (150 mM NaCl, 10 mM Tris pH 8, 0.3% NP-40, 1 mM DTT, 0.25% BSA and 0.5 mM phenylmethylsulfonyl fluoride) for 2 hours at 4° C. The beads were subsequently washed twice in GST interaction buffer containing BSA, followed by two more washes in GST interaction buffer without BSA. Finally, the bound BRCA1 C-terminal polypeptide was eluted by boiling the beads for 5 min in 30 µl loading buffer and analysed by SDS-PAGE.

Northern Blot Analysis

Poly(A)$^+$ RNA was isolated from human and mouse breast epithelial cell lines cited in previous studies (Douglas, A. M., Grant, S. L., Goss, G. A., Clouston, D. R., Sutherland, R. L., and Begley, C. G. (1998) *Int J Cancer* 75(1), 64-73) and Northern analysis was performed (Visvader, J. E., Elefanty, A. G., Strasser, A., and Adams, J. M. (1992) *Embo J* 11(12), 4557-64).

Transactivation Assays in Yeast and Mammalian Cells

The yeast transcription assay was performed in the yeast strain BJ5462; this was cotransformed with the LacZ reporter plasmid, YepΔ62 (generously provided by P. Vaughan), and pGBT9-BRCA1(AD), and colonies selected on media deficient in leu and trp. These transformants were then additionally transformed with either the pYX212-LMO4 expression plasmid or empty vector, and were selected on media lacking ura, trp and leu. β-galactosidase activities were determined using the o-nitrophenyl-β-D-galactoside (ONPG) liquid culture assay following standard protocol (CLONTECH Yeast Protocols Handbook).

Kidney embryonal 293T cells were transiently transfected (6-well plates) with the indicated plasmids: 0.5 µg pG5CAT (CLONTECH), 1 µg pCMV-Gal4b-BRCA1-AD or 1 µg Gal4b parental vector, and either 2 µg Flag-EF1α-LMO4 or 2 µg empty control vector using the calcium phosphate precipitation method. CAT activity was determined using the CAT Elisa system (Roche) and was normalised against protein concentration, as determined by the Bradford assay (Bio-Rad).

EXAMPLE 6

Identification of CTIP as a LMO4-Interacting Protein

We used the yeast two-hybrid system to identify LMO4-interacting proteins in breast epithelium. A screen of 8.4×10$^6$ transformants of a primary breast adenocarcinoma cDNA library yielded more than 800 His$^+$ colonies. Six hundred and fifty-nine P-galactosidase positive clones were isolated and sequentially screened by yeast colony hybridisation using cDNA probes representing the known LMO4-associated proteins, Ldb1 and Deformed Epidermal Autoregulatory Factor (DEAF 1) (Kenny, D. A., Jurata, L. W., Saga, Y., and Gill, G. N. (1998) *Proc Natl Acad Sci USA* 95(19), 11257-62;Sugihara, T. M., Bach, I., Kioussi, C., Rosenfeld, M. G., and Andersen, B. (1998) *Proc Natl Acad Sci USA* 95(26), 15418-23;Grutz, G., Forster, A., and Rabbitts, T. H. (1998) *Oncogene* 17(21), 2799-803), and known false positives. Approximately 60% of these clones corresponded to Ldb1/Ldb2 (30%) or DEAF1 (30%). Of 150 cDNA clones sequenced, 22 were found to correspond to either Ldb1 or Ldb2, 20 encoded DEAF1, at least 70 corresponded to false positives (e.g. ribosomal, mitochondrial and extracellular matrix proteins), while the remaining 38 cDNAs represented 9 distinct genes or ESTs. One of these clones corresponded to the complete coding sequence of CtIP (CtBP interacting protein), which encodes a cofactor originally identified on the basis of its interaction with the transcriptional corepressor CtBP (Adenovirus EIA C-terminal binding protein) (Schaeper, U., Subramanian, T., Lim, L., Boyd, J. M., and Chinnadurai, G. (1998) *J Biol Chem* 273(15), 8549-52).

EXAMPLE 7

In Vivo Association Between LMO4 and CTIP

Figure 6:
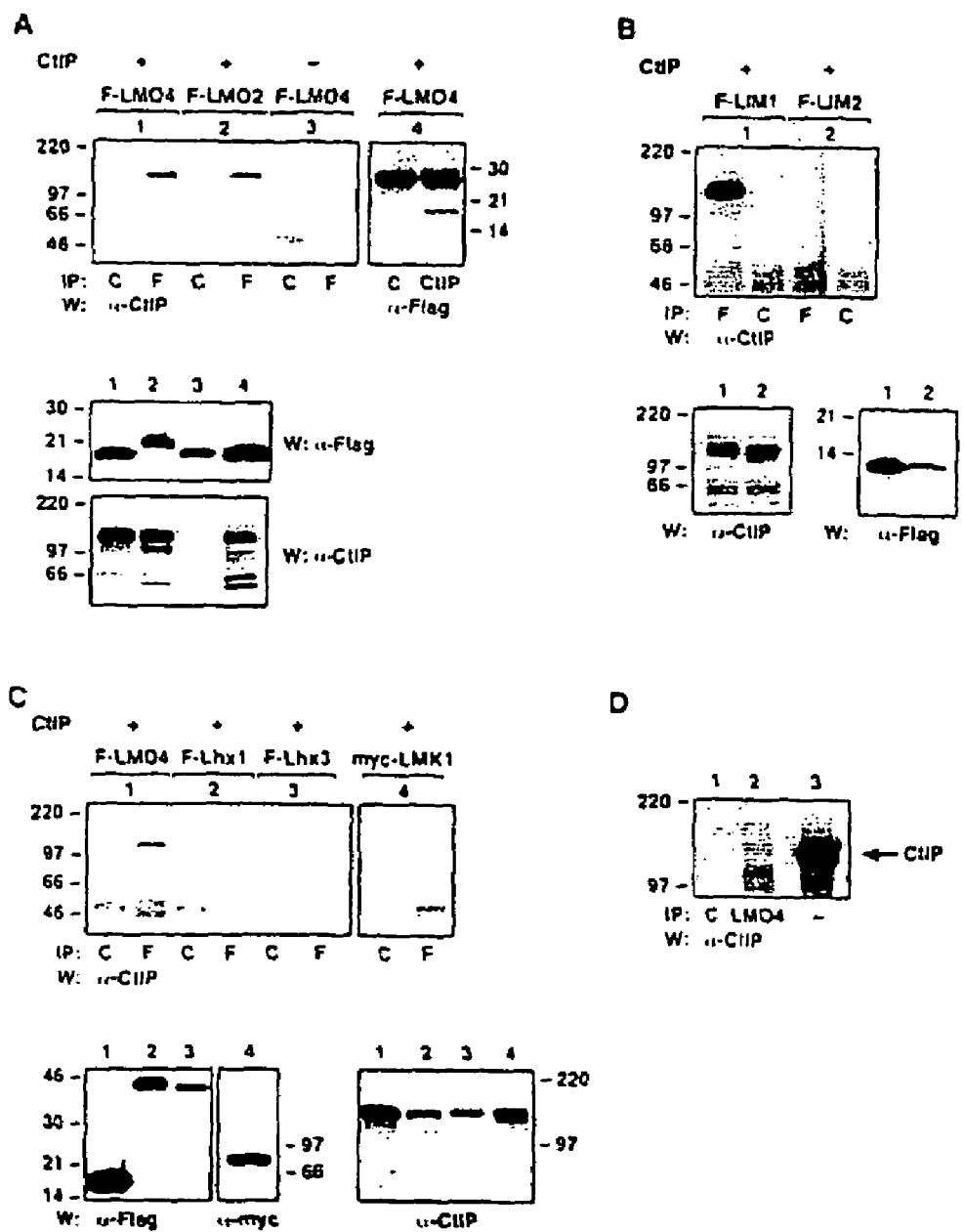
FIG. 6: Interaction between LM04 and CtIP requires a single LIM domain and appears to be specific for the LMO subclass. A, CtIP associates with LMO4 and LMO2. 293T cells were transfected with expression constructs encoding Flag-tagged derivatives of LMO4 (lanes 1, 3 and 4) or LMO2 (lane 2), together with that encoding CtIP. Lysates were prepared and proteins immunoprecipitated with the indicated specific antisera. F, Flag; C, control isotype-matched monoclonal antibody. Immunoblotting was performed with the antibodies indicated under each panel. Lane 4 depicts the reciprocal immunoprecipitation experiment performed using an anti-CtIP antibody. The 25 kD bands in lane 4 represent light chain. Western blot analysis of lysates confirmed expression of CtIP and LMO proteins. Note the different size markers indicated for LMO proteins detected by western analysis using anti-Flag antibody (lane 4). B, The first LIM domain but not the second LIM domain of LMO4 interacts with CtIP. 293T cells were transfected with expression constructs encoding Flag-tagged derivatives of LIM1 (lane 1) or LIM2 (lane 2), in the presence of plasmid encoding CtIP. Cell extracts were immunoprecipitated with anti-Flag (F) antibody, then immunoblotted with anti-CtIP antisera. Western blot analysis of lysates confirmed expression of CtIP and LIM polypeptides (lower panels). C, Heterologous LIM proteins do not interact with CtIP. 293T cells were transfected with expression constructs encoding Flag-tagged derivatives of LMO4 (lane 1), Lhx1 (lane 2), Lhx3 (lane 3), or myc-tagged LMK1 (lane 4), in the presence of plasmid encoding CtIP. Cell extracts were immunoprecipitated with anti-Flag (F) antibody, then immunoblotted with anti-CtIP antibody. Western blot analysis of lysates confirmed expression of CtIP and LIM proteins (lower panels). D, Interaction between endogenous LMO4 and CtIP proteins in HBL100 epithelial cells. Nuclear extracts were immunoprecipitated with pre-immune serum (lane 1) or anti-LMO4 antisera (lane 2), then blotted using anti-CtIP monoclonal antibody. Nuclear extract from these cells was loaded in an adjacent lane to provide a size control for CtIP (lane 3).

A specific interaction between CtIP and LMO4 was confirmed in mammalian cells. Expression vectors encoding LMO4, LMO2 or heterologous LIM domain proteins, each carrying a Flag- or myc-epitope at the N-terminus, together with an expression vector harboring CtIP (residues 45-897), were transiently transfected into 293T cells. Whole cell extracts were analysed using a coupled coimmunoprecipitation/western blot assay. As shown in FIG. 6A, Flag-LMO4 and CtIP were found to specifically associate in vivo, in reciprocal co-immunoprecipitation experiments (lanes 1 and 4). CtIP was not detected in immunoprecipitates from cells expressing Flag-LMO4 alone (lane 3) or in those using an isotype-matched control antibody. A single LIM domain of LMO4 (amino acids 1-82) was found to be sufficient to mediate interaction with CtIP in mammalian cells (FIG. 6B, lane 1). Only the first LIM domain of LMO4 but not the second LIM domain (amino acids 79-165) could associate with CtIP (lane 2). CtIP also coprecipitated with the related LIM domain protein, LMO2 (5) (FIG. 6A, lane 2), but not with the nuclear LIM homeodomain proteins Lhx1 and Lhx3 (FIG. 6C, lanes 2 and 3), nor with LIM-kinase (LMK1) (FIG. 6C, lane 4).

To test the interaction between endogenous proteins in breast epithelial cells, we generated a rabbit polyclonal antiserum against full-length mouse LMO4. This antiserum recognises a protein of about 17 kD in breast epithelial cells and in cells transfected with an LMO4 expression vector. Nuclear extracts from HBL100 cells were immunoprecipitated with anti-LMO4 antiserum (FIG. 6D, lane 2) or pre-immune serum (lane 1). Immunoblotting with a mouse anti-CtIP monoclonal antibody revealed a specific band of 125 kD (FIG. 6D), thus confirming the in vivo association between native CtIP and LMO4 proteins.

EXAMPLE 8

Coexpression of LMO4 and CTIP in Breast Epithelial Cell Lines and Subcellular Localisation of LMO4

Both the LMO4 and CtIP genes have been reported to be expressed in a number of different tissues and cell types (Kenny, D. A., Jurata, L. W., Saga, Y., and Gill, G. N. (1998) *Proc Natl Acad Sci USA* 95(19),11257-62; Sugihara, T. M., Bach, I., Kioussi, C., Rosenfeld, M. G., and Andersen, B. (1998) *Proc Natl Acad Sci USA* 95(26), 15418-23; Wong, A. K., Ormonde, P. A., Pero, R., Chen, Y., Lian, L., Salada, G., Berry, S., Lawrence, Q., Dayananth, P., Ha, P., Tavtigian, S. V., Teng, D. H., and Bartel, P. L. (1998) *Oncogene* 17(18), 2279-85). We surveyed their expression in a panel of breast epithelial cell lines, the majority of which were derived from human breast cancers but also included immortalised human cells (184). Northern analysis revealed CtIP RNA (3.6 kb) levels were relatively uniform while expression of the LMO4 transcripts (1.8 and 2.3 kb) varied dramatically (FIG. 8). High levels of LMO4 were apparent in a number of human breast cancer cell lines, including BT-549, BT-474, HS-578T, MDA-MB361, T-47D and ZR-75B (FIG. 8), relative to the low levels evident in the immortalised 184 cells, as we recently reported (Visvader, J. E., Venter, D., Hahm, K., Santamaria, M., Sum, E. Y. M., O'Reilly, L., White, D., Williams, R., Armes, J., and Lindeman, G. J. (2001) *Proc Natl Acad Sci USA* 98(25), 14452-14457). In human breast cancers, overexpression of the LMO4 gene has been observed at both the RNA and protein levels (Visvader, J. E., Venter, D., Hahm, K., Santamaria, M., Sum, E. Y. M., O'Reilly, L., White, D., Williams, R., Armes, J., and Lindeman, G. J. (2001) *Proc Natl Acad Sci USA* 98(25), 14452-14457).

EXAMPLE 9

LMO4 Interacts with Two Distinct Domains in CTIP

The function of CtIP is not known but it appears to serve as a cofactor for several nuclear regulatory proteins, including BRCA1, Adenovirus EIA C-terminal binding protein (CtBP), Retinoblastoma (Rb) and p130 pocket proteins (Yu, X., Wu, L. C., Bowcock, A. M., Aronheim, A., and Baer, R. (1998) *J Biol Chem* 273(39), 25388-92;Wong, A. K., Ormonde, P. A., Pero, R., Chen, Y., Lian, L., Salada, G., Berry, S., Lawrence, Q., Dayananth, P., Ha, P., Tavtigian, S. V., Teng, D. H., and Bartel, P. L. (1998) *Oncogene* 17(18), 2279-85;Li, S., Chen, P. L., Subramanian, T., Chinnadurai, G., Tomlinson, G., Osborne, C. K., Sharp, Z. D., and Lee, W. H. (1999) *J Biol Chem* 274(16), 11334-8, 30-32). In addition to the defined regions that interact with these proteins, CtIP contains two potential leucine zipper domains (120-141 and 740-761) (Fusco, C., Reymond, A., and Zervos, A. S. (1998) Genomics 51(3), 351-8), depicted in FIG. 7A. To delineate the domains within CtIP that mediate interaction with LMO4, a series of CtIP deletion mutants (FIG. 7A), each linked to an N-terminal HA-epitope tag, were co-transfected with Flag-LMO4 into 293T epithelial cells. As shown in FIG. 8B, HA-CtIP (45-371), HA-CtIP (371-897), HA-CtIP (45-897) and HA-CtIP (620-897) proteins could associate with Flag-LMO4 (lanes 2, 4, 5, and 6). In contrast, neither the HA-CtIP (59-320) nor HA-CtIP (281-620) mutants were immunoprecipitable by an anti-Flag antibody (lanes 1 and 3, respectively). Thus, there are apparently two regions within CtIP that can mediate interaction with LMO4: a small domain at the N-terminus (residues 45-59) and a C-terminal region (residues 620-897), which encompasses a putative leucine zipper motif (FIG. 8A). These regions are distinct from those that associate with CtBP (amino acids 392-396), Rb (153-157) and BRCA1 (133-369) (Yu, X., Wu, L. C., Bowcock, A. M., Aronheim, A., and Baer, R. (1998) *J Biol Chem* 273(39), 25388-92;Yu, X., and Baer, R. (2000) *J Biol Chem* 275(24), 18541-9Schaeper, U., Subramanian, T., Lim, L., Boyd, J. M., and Chinnadurai, G. (1998) *J Biol Chem* 273(15), 8549-52;Fusco, C., Reymond, A., and Zervos, A. S. (1998) *Genomics* 51(3), 351-8; Meloni, A. R., Smith, E. J., and Nevins, J. R. (1999) *Proc Natl Acad Sci USA* 96(17),9574-9).

EXAMPLE 10

LMO4 Also Interacts with the Breast and Ovarian Tumor Suppressor BRCA1

Since CtIP was recently demonstrated to interact with the breast tumor suppressor BRCA1 (Yu, X., Wu, L. C., Bowcock, A. M., Aronheim, A., and Baer, R. (1998) *J Biol Chem* 273(39), 25388-92;Wong, A. K., Ormonde, P. A., Pero, R., Chen, Y., Lian, L., Salada, G., Berry, S., Lawrence,. Q., Dayananth, P., Ha, P., Tavtigian, S. V., Teng, D. H., and Bartel, P. L. (1998) *Oncogene* 17(18), 2279-85; Li, S., Chen, P. L., Subramanian, T., Chinnadurai, G., Tomlinson, G., Osborne, C. K., Sharp, Z. D., and Lee, W. H. (1999) *J Biol Chem* 274(16), 11334-8), we investigated whether LMO4, CtIP and BRCA1 could participate in a multiprotein complex. Both CtIP and LMO4 were co-immunoprecipitated with an anti-myc antibody from 293T cells expressing myc-tagged BRCA1, Flag-tagged LMO4 and CtIP (FIG. 9A, lane 2). This finding revealed that all three proteins can form a stable multiprotein complex in vivo. The presence of exogenous CtIP was not necessary for immunoprecipitation of LMO4 by the anti-myc antibody, as shown in FIG. 9A (lane 1). These results raised the possibility that LMO4 might directly associate with BRCA1 (see below).

To further examine this interaction in epithelial cells, a rat anti-LMO4 monoclonal antibody was used to immunoprecipitate proteins from HBL100-derived nuclear extracts. This antibody specifically recognises a 17 kD protein in cells transfected with a LMO4 expression vector but not in those lacking LMO4. Endogenous BRCA1 was immunoprecipitated by the anti-LMO4 monoclonal antibody (FIG. 9B, lane 2), but not with a control antibody (FIG. 9B, lane 3). This result confirms an in vivo association between LMO4 and BRCA1 and, moreover, demonstrates that this interaction occurs between native proteins in epithelial cells. Immunoblotting of the anti-LMO4 immunoprecipitated protein with anti-CtIP monoclonal antibody yielded a faint band of 125 kD, corresponding to CtIP (FIG. 9B, middle panel), while blotting with anti-LMO4 antibody gave rise to the expected 17 kD LMO4 protein (FIG. 9B, lower panel). Thus LMO4, BRCA1 and CtIP have the potential to form a native complex in vivo.

We investigated whether the nuclear adaptor protein Ldb1, which binds LMO4 and other LIM proteins with high affinity (Kenny, D. A., Jurata, L. W., Saga, Y., and Gill, G. N. (1998) *Proc Natl Acad Sci USA* 95(19), 11257-62; Sugihara, T. M., Bach, I., Kioussi, C., Rosenfeld, M. G., and Andersen, B. (1998) *Proc Natl Acad Sci USA* 95(26), 15418-23; Grutz, G., Forster, A., and Rabbitts, T. H. (1998) *Oncogene* 17(21), 2799-803), could also participate in the multiprotein complex. Ldb1 could be immunoprecipitated from cells transfected with plasmids encoding CtIP, BRCA1, LMO4 and LDB1 using an anti-CtIP antibody (FIG. 9C). Therefore, all four proteins have the potential to form a stable complex in vivo.

EXAMPLE 11

The BRCT Domain of BRCA1 Directly Interacts with LMO4

The C-terminal 335 amino acids of BRCA1 (SZ fragment, residues 1528-1863) were sufficient to mediate interaction with LMO4 (FIG. 10A) in transfected cells. This region encompasses two tandem BRCT motifs that are required for BRCA1 function in the suppression of tumorigenesis (Yu, X., Wu, L. C., Bowcock, A. M., Aronheim, A., and Baer, R. (1998) *J Biol Chem* 273(39), 25388-92;Wong, A. K., Ormonde, P. A., Pero, R., Chen, Y., Lian, L., Salada, G., Berry, S., Lawrence, Q., Dayananth, P., Ha, P., Tavtigian, S. V., Teng, D. H., and Bartel, P. L. (1998) *Oncogene* 17(18), 2279-85;Li, S., Chen, P. L., Subramanian, T., Chinnadurai, G., Tomlinson, G., Osborne, C. K., Sharp, Z. D., and Lee, W. H. (1999) *J Biol Chem* 274(16), 11334-8). We confirmed the association between LMO4 and BRCA1 using an in vitro binding assay. Full-length LMO4 expressed as a glutathione-S-transferase (GST) fusion protein, immobilised on glutathione sepharose beads, was incubated with in vitro translated, $^{35}$S-methionine-labeled BRCA1-SZ polypeptide (1528-1863). As shown in FIG. 10B, BRCA1 specifically associated with GST-LMO4, but failed to interact with GST alone.

To exclude the possibility that CtIP was acting as a bridging molecule between LMO4 and BRCA1, we tested the interaction between BRCA1 and LMO4 in yeast. It is notable that CtIP appears to be absent from the *S. cerevisiae* genome (*Saccharomyces* Genome Database, NCBI). Cotransformation of Hf7c cells with the SZ portion of BRCA1 linked to the Gal4-activation domain and GBT9-LMO4, revealed a direct association between these proteins (FIG. 10C). His$^+$ β-Gal$^+$ colonies were obtained for these transformants, as was observed for yeast cells cotransformed with LMO4 and CtIP. Thus, the BRCT domains of BRCA1 mediate direct binding to both LMO4 and CtIP.

EXAMPLE 12

Tumor-Derived Mutations of BRCA1 Do Not Affect LM04 Binding

Figure 11:
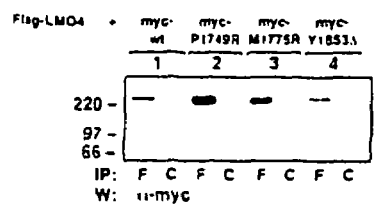
FIG. 11: Tumor-associated mutants of BRCA1 interact with LMO4. 293T cells were transfected with expression constructs encoding Flag-tagged LMO4 together with myc-tagged wild-type BRCA1 (lane 1) or mutants of BRCA1 (lanes 2-4). Lysates were prepared and proteins immunoprecipitated with anti-Flag (F) or control (C) monoclonal antibody. Immunoblotting with anti-myc antibody revealed interactions between LMO4 and all BRCA1-derivatives.

Tumor-associated mutations have been identified in a significant proportion of hereditary breast cancer patients. The lesions include missense mutations (P1749R, M1775R) and a nonsense mutation (Y1853Δ) that deletes the C-terminal 11 amino acids of BRCA1 (Yu, X., Wu, L. C., Bowcock, A. M., Aronheim, A., and Baer, R. (1998) *J Biol Chem* 273(39), 25388-92;Li, S., Chen, P. L., Subramanian, T., Chinnadurai, G., Tomlinson, G., Osborne, C. K., Sharp, Z. D., and Lee, W. H. (1999) *J Biol Chem* 274(16), 11334-8). These tumor-associated mutations have been demonstrated to abolish binding of BRCA1 to CtIP (Yu, X., Wu, L. C., Bowcock, A. M., Aronheim, A., and Baer, R. (1998) *J Biol Chem* 273(39), 25388-92;Li, S., Chen, P. L., Subramanian, T., Chinnadurai, G., Tomlinson, G., Osborne, C. K., Sharp, Z. D., and Lee, W. H. (1999) *J Biol Chem* 274(16), 11334-8). To assess their effect on BRCA1-LMO4 interaction, myc-tagged BRCA1 expression constructs containing these mutations were tested for their ability to bind Flag-tagged LMO4 in 293T cells. All mutants were found to interact with LMO4, as observed for the wild-type BRCA1 polypeptide (FIG. 11). Thus, mutations occurring within BRCA1 in hereditary breast cancer patients can abolish CtIP binding without affecting interaction between BRCA1 and LMO4.

EXAMPLE 13

LM04 Represses the Transcriptional Activity of BRCA1

Figure 12:
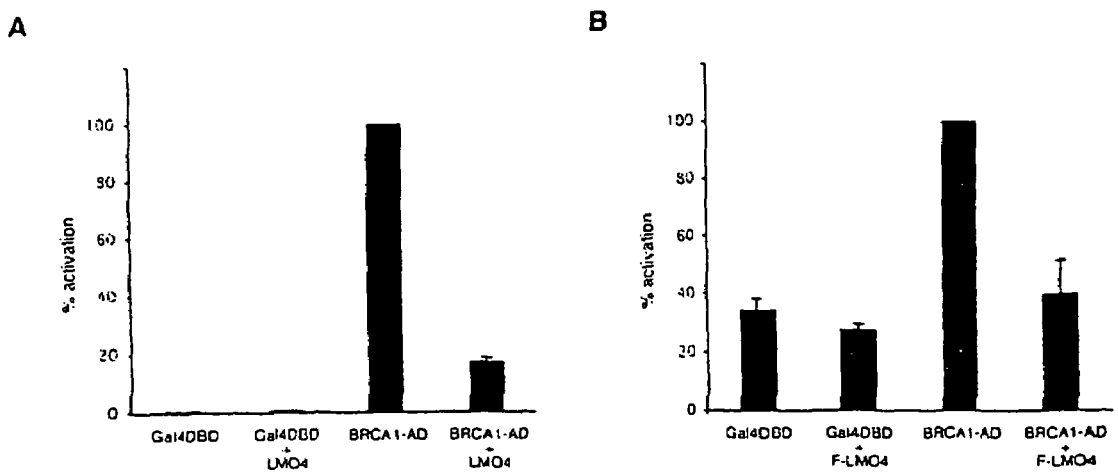
FIG. 12: LMO4 represses BRCA1 activity in both yeast and mammalian transcriptional activation assays. A, Activation of β-galactosidase expression in BJ5462 cells expressing either GAL4-DBD (DNA-binding domain) or GAL4-BRCA1-AD (activation domain) fusion protein in the presence or absence of a yeast LMO4 expression vector. Transcriptional activity is expressed relative to that of the BRCA1-AD domain, which was designated to be 100%. B, Activity of the BRCA1 activation domain in 293T cells cotransfected with the pG5CAT reporter plasmid, containing five Gal binding sites upstream of the chloramphenicol acteyltransferase gene, and either an LMO4 expression construct or empty vector. The BRCA1-AD domain was fused to the GAL4-DBD. Basal activity of the GAL4-DBD is shown in both yeast and mammalian cells. The data in A and B represent an average of three independent experiments with standard error of the mean indicated. Western blot analysis confirmed expression of the relevant proteins, designated by arrows, in yeast or mammalian cells.
Figure 12:
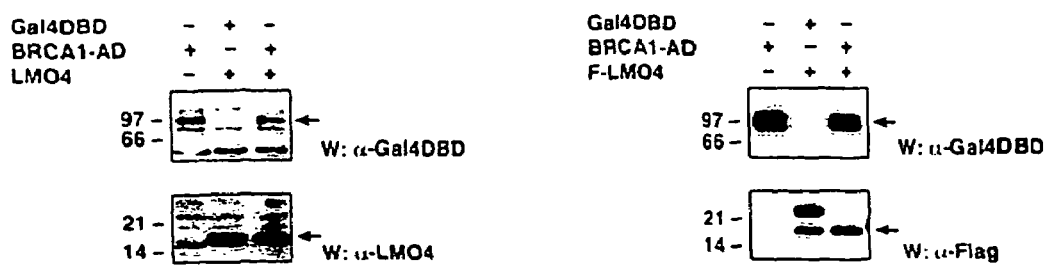
Figure 13:
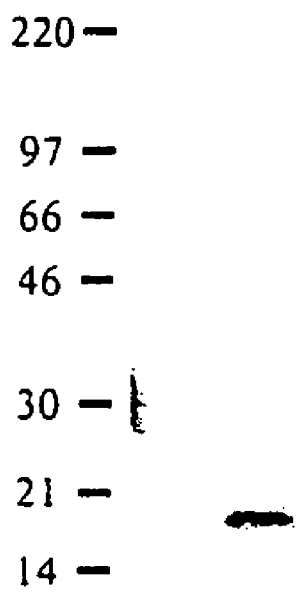
FIG. 13: Western blot analysis of LMO4 expression in mouse tissue. Tissue lysates were prepared from wild-type and LMO4 knock-out e16.5 mouse embryos and normalised for total protein content. 50 μg of each lysate was subjected to SDS-PAGE and then immunoblotted with anti-LMO4 mAB 20F8 (A) or 16H2 (B).
Figure 13:
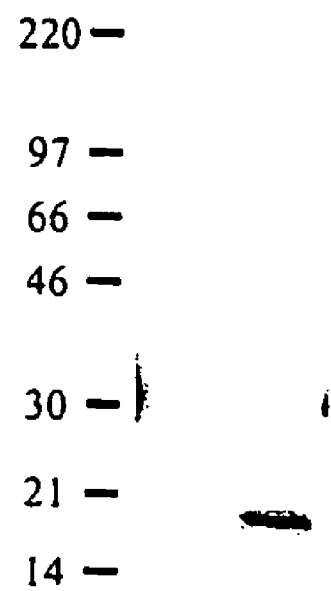
Figure 14:
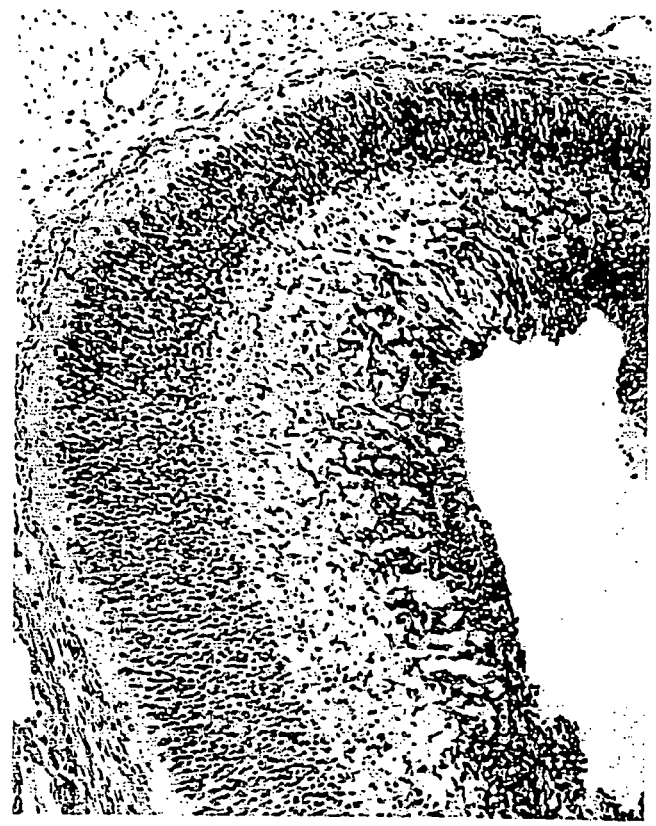
FIG. 14: Expression of LMO4 in the developing mouse brain at e16.5. Immunostaining was performed on formalin-fixed wild-type (A) and LMO4 knock-out (B) embryo sections with anti-LMO4 mAB 20F8.
Figure 14:
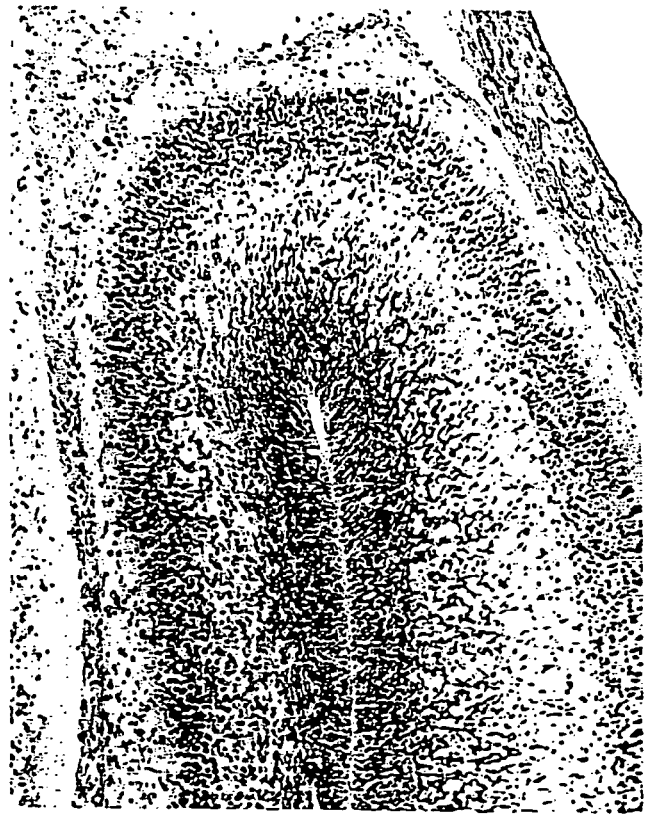
Figure 15:
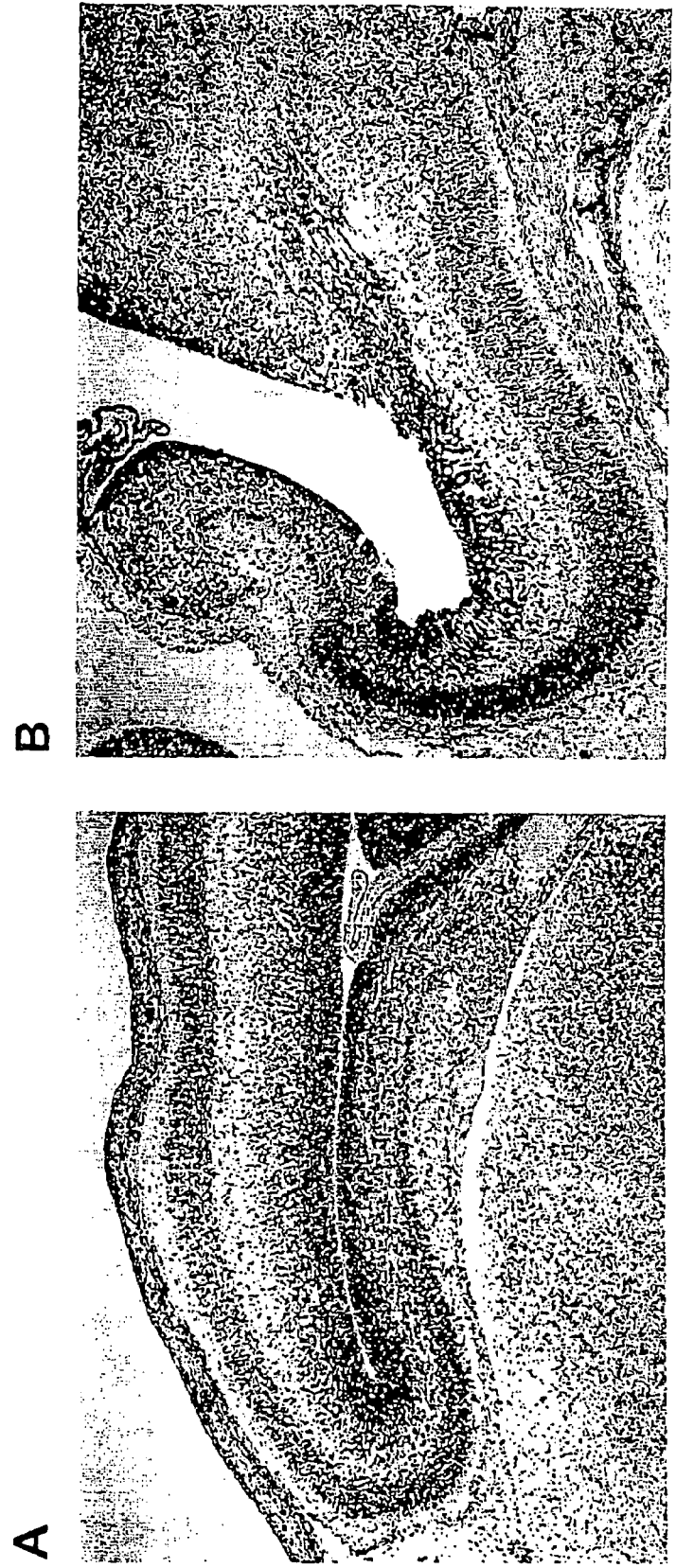
FIG. 15: Expression of LMO4 in the developing mouse brain at e16.5. Immunostaining was performed on formalin-fixed wild-type (A) and LMO4 knock-out (B) embryo sections with anti-LMO4 mAB 16H2.

The BRCA1 C-terminal (BRCT) domain has previously been shown to activate transcription when recruited to a promoter via a heterologous DNA-binding domain (Chapman, M. S., and Verma, I. M. (1996) *Nature* 382(6593), 678-9; 34). Further characterisation of the C-terminus has revealed that there are two adjacent activation domains, AD1 (residues 1293-1558) and AD2 (residues 1560-1863), which together constitute the AD domain of 571 amino acids (Hu, Y. F., Miyake, T., Ye, Q., and Li, R. (2000) *J Biol Chem* 275(52), 40910-5). Functional synergy occurs between AD1 and AD2 in both yeast and mammalian cells, such that the AD region is a stronger transcriptional activator than either domain alone (Hu, Y. F., Miyake, T., Ye, Q., and Li, R. (2000) *J Biol Chem* 275(52), 40910-5). To explore the effect of LMO4 on activation of transcription by BRCA1, we initially used a yeast-based transcription assay with the C-terminal AD region of BRCA1 fused to the Gal4 DNA-binding domain. This plasmid was introduced with either a LMO4 yeast expression vector or an empty vector into the BJ5462 yeast strain, harboring a LacZ reporter plasmid. BRCA1-AD was a potent transactivator, inducing transcription 400- to 600-fold over basal Gal4 DNA-binding activity (FIG. 12A). This activation was markedly repressed by LMO4, which resulted in an 80% reduction in the level of activation by BRCA1-AD (FIG. 12A). The expression of BRCA1-AD was equivalent in the presence or absence of the LMO4-encoding plasmid (FIG. 12A, lower panel).

To confirm the findings of the yeast transcription assay, we performed a similar study in mammalian 293T cells. BRCA1-AD tethered to the Gal4 DNA-binding domain induced transcription of the Gal4-CAT reporter gene by 3- to 4-fold over the basal activity of the Gal4-DNA-binding domain alone (FIG. 12B). Consistent with the findings above, LMO4 exerted a negative effect on transactivation by BRCA1 (approximately 3-fold), returning transcriptional activity to the basal level observed with the Gal4 DNA-binding domain (DBD) alone. LMO4 does not act as a general repressor since the activity of the VP16 transactivation domain was not altered by forced LMO4 expression (data not shown). Moreover, the basal activity of the Gal4 DBD was not reduced by the presence of LMO4 (FIG. 12B). The expression of BRCA1-AD was unaffected by the presence of LMO4 (FIG. 12B, lower panel).

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

Agulnick, A. D., Taira, M., Breen, J. J., Tanaka, T., Dawid, I. B. & Westphal, H. (1996) Nature 384, 270-2.

Armes, J. E., Trute, L., White, D., Southey, M. C., Hammet, F., Tesoriero, A., Hutchins, A. M., Dite, G. S., McCredie, M. R., Giles, G. G., Hopper, J. L. & Venter, D. J. (1999) Cancer Res 59, 2011-7.

Bach, I. (2000) *Mech Dev* 91(1-2), 5-17

Bach, I., Carriere, C., Ostendorff, H. P., Andersen, B. & Rosenfeld, M. G. (1997) Genes Dev 11, 1370-80.

Bach, I., Rhodes, S. J., Pearse, R. V., 2nd, Heinzel, T., Gloss, B., Scully, K. M., Sawchenko, P. E., and Rosenfeld, M. G. (1995) *Proc Natl Acad Sci USA* 92(7), 2720-4

Bärlund; M., Tirkkonen, M., Forozan, F., Tanner, M. M., Kallioniemi, O. & Kallioniemi, A. (1997) Genes Chromosomes Cancer 20, 372-6.

Boehm, T., Baer, R., Lavenir, I., Forster, A., Waters, J. J., Nacheva, E. & Rabbitts, T. H. (1988) Embo J 7, 385-94.

Boehm, T., Foroni, L., Kaneko, Y., Perutz, M. F. & Rabbitts, T. H. (1991) Proc Natl Acad Sci USA 88, 4367-71.

Byrne, J. A., Nourse, C. R., Basset, P., and Gunning, P. (1998) *Oncogene* 16(7), 873-81

Catteau, A., Harris, W. H., Xu, C. F., and Solomon, E. (1999) *Oncogene* 18(11), 1957-65

Chapman, M. S., and Verma, I. M. (1996) *Nature* 382(6593), 678-9

Couch, F. J., and Weber, B. L. (1996) *Hum Mutat* 8(1), 8-18

Cuny, M., Kramar, A., Courjal, F., Johannsdottir, V., Iacopetta, B., Fontaine, H., Grenier, J., Culine, S. & Theillet, C. (2000) Cancer Res 60, 1077-83.

Dawid, I. B., Breen, J. J., and Toyama, R. (1998) *Trends Genet* 14(4), 156-62

Deng, C. X., and Brodie, S. G. (2000) *Bioessays* 22(8), 728-37

Desprez, P.-Y., Roskelley, C., Campisi, J. & Bissell, M. J. (1993) Mol. Cell. Diff. 1, 99-110.

Dobrovic, A., and Simpfendorfer, D. (1997) *Cancer Res* 57(16), 3347-50

Douglas, A. M., Grant, S. L., Goss, G. A., Clouston, D. R., Sutherland, R. L., and Begley, C. G. (1998) *Int J Cancer* 75(1), 64-73, Emi, M., Matsumoto, S., Iida, A., Tsukamoto, K., Nakata, T., Yokota, T., Akiyama, F., Sakamoto, G., Yoshimoto, M., Kasumi, F. & Nakamura, Y. (1997) Breast Cancer 4, 243-246.

Fisch, P., Boehm, T., Lavenir, I., Larson, T., Arno, J., Forster, A. & Rabbitts, T. H. (1992) Oncogene 7, 2389-97.

Fusco, C., Reymond, A., and Zervos, A. S. (1998) *Genomics* 51(3), 351-8

Futreal, P. A., Soderkvist, P., Marks, J. R., Iglehart, J. D., Cochran, C., Barrett, J. C., and Wiseman, R. W. (1992) *Cancer Res* 52(9), 2624-7

German, M. S., Wang, J., Chadwick, R. B., and Rutter, W. J. (1992) *Genes Dev* 6(11), 2165-76

Grutz, G., Forster, A. & Rabbitts, T. H. (1998) Oncogene 17, 2799-803.

Grutz, G., Forster, A., and Rabbitts, T. H. (1998) *Oncogene* 17(21),2799-803

Hoggard, N., Brintnell, B., Howell, A., Weissenbach, J. & Varley, J. (1995) Genes Chromosomes Cancer 12, 24-31.

Hu, Y. F., Hao, Z. L., and Li, R. (1999) *Genes Dev* 13(6), 637-42

Hu, Y. F., Miyake, T., Ye, Q., and Li, R. (2000) *J Biol Chem* 275(52), 40910-5

Huang, D. C., Cory, S., and Strasser, A. (1997) *Oncogene* 14(4), 405-14

Jurata, L. W., and Gill, G. N. (2000), pp. 75-113

Jurata, L. W., Kenny, D. A., and Gill, G. N. (1996) *Proc Natl Acad Sci USA* 93(21), 11693-8

Kallioniemi, A., Kallioniemi, O. P., Piper, J., Tanner, M., Stokke, T., Chen, L., Smith, H. S., Pinkel, D., Gray, J. W. & Waldman, F. M. (1994) Proc Natl Acad Sci USA 91, 2156-60.

Kenny, D. A., Jurata, L. W., Saga, Y., and Gill, G. N. (1998) *Proc Natl Acad Sci USA* 95(19), 11257-62

Knuutila, S., Bjorkqvist, A. M., Autio, K., Tarkkanen, M., Wolf, M., Monni, O., Szymanska, J., Larramendy, M. L., Tapper, J., Pere, H., El-Rifai, W., Hemrner, S., Wasenius, V. M., Vidgren, V. & Zhu, Y. (1998) Am J Pathol 152, 1107-23.

Koonin, E. V., Altschul, S. F., and Bork, P. (1996) *Nat Genet* 13(3), 266-8

Li, S., Chen, P. L., Subramanian, T., Chinnadurai, G., Tomlinson, G., Osborne, C. K., Sharp, Z. D., and Lee, W. H. (1999) *J Biol Chem* 274(16), 11334-8

Mancini, D. N., Rodenhiser, D. I., Ainsworth, P. J., O'Malley, F. P., Singh, S. M., Xing, W., and Archer, T. K. (1998) *Oncogene* 16(9), 1161-9

McGuire, E. A., Rintoul, C. E., Sclar, G. M. & Korsmeyer, S. J. (1992) Mol Cell Biol 12, 4186-96.

Meloni, A. R., Smith, E. J., and Nevins, J. R. (1999) *Proc Natl Acad Sci USA* 96(17), 9574-9

Miki, Y., Swensen, J., Shattuck-Eidens, D., Futreal, P. A., Harshman, K., Tavtigian, S., Liu, Q., Cochran, C., Bennett, L. M., Ding, W., and et al. (1994) *Science* 266(5182), 66-71

Monteiro, A. N. (2000) *Trends Biochem Sci* 25(10), 469-74

Neale, G. A., Rehg, J. E. & Goorha, R. M. (1997) Leukemia 11 Suppl 3, 289-90.

Nicholson, S. E., Willson, T. A., Farley, A., Starr, R., Zhang, J. G., Baca, M., Alexander, W. S., Metcalf, D., Hilton, D. J. & Nicola, N. A. (1999) EMBO J 18, 375-85.

Pinkel, D., Segraves, R., Sudar, D., Clark, S., Poole, I., Kowbel, D., Collins, C., Kuo, W. L., Chen, C., Zhai, Y., Dairkee, S. H., Ljung, B. M., Gray, J. W. & Albertson, D. G. (1998) Nat Genet 20, 207-11.

Rabbitts, T. H. (1998) *Genes Dev* 12(17), 2651-7

Racevskis, J., Dill, A., Sparano, J. A., and Ruan, H. (1999) *Biochim Biophys Acta* 1445(1), 148-53

Rice, J. C., Massey-Brown, K. S., and Futscher, B. W. (1998) *Oncogene* 17(14), 1807-12

Royer-Pokora, B., Loos, U. & Ludwig, W. D. (1991) Oncogene 6, 1887-93.

Russell, A., Thompson, M. A., Hendley, J., Trute, L., Arrnes, J. & Germain, D. (1999) Oncogene 18, 1983-91.

Sanchez-Garcia, I., and Rabbitts, T. H. (1994) *Trends Genet* 10(9), 315-20

Sanchez-Garcia, I., Osada, H., Forster, A., and Rabbitts, T. H. (1993) *Embo J* 12(11), 4243-50

Schaeper, U., Subramanian, T., Lim, L., Boyd, J. M., and Chinnadurai, G. (1998) *J Biol Chem* 273(15), 8549-52

Schmutzler, R. K., Bierhoff, E., Werkhausen, T., Fimmers, R., Speiser, P., Kubista, E., Krebs, D., Zeillinger, R., Wiestler, O. D., and Von Deimling, A. (1997) *Int J Cancer* 74(3), 322-5

Scully, R., and Livingston, D. M. (2000) *Nature* 408(6811), 429-32

Scully, R., Anderson, S. F., Chao, D. M., Wei, W., Ye, L., Young, R. A., Livingston, D. M., and Parvin, J. D. (1997) *Proc Natl Acad Sci USA* 94(11), 5605-10

Scully, R., Chen, J., Plug, A., Xiao, Y., Weaver, D., Feunteun, J., Ashley, T., and Livingston, D. M. (1997) *Cell* 88(2), 265-75

Shattuck-Eidens, D., McClure, M., Simard, J., Labrie, F., Narod, S., Couch, F., Hoskins, K., Weber, B., Castilla, L., Erdos, M., and et al. (1995) *Jama* 273(7), 535-41

Smith, D. B., and Johnson, K. S. (1988) *Gene* 67(1), 31-40

Sugihara, T. M., Bach, I., Kioussi, C., Rosenfeld, M. G., and Andersen, B. (1998) *Proc Natl Acad Sci USA* 95(26), 15418-23

Taira, M., Otani, H., Saint-Jeannet, J. P., and Dawid, I. B. (1994) *Nature* 372(6507), 677-9 Thompson, M. E., Jensen, R. A., Obermiller, P. S., Page, D. L., and Holt, J. T. (1995) *Nat Genet* 9(4), 444-50

Tse, E., Grutz, G., Gamer, A. A., Ramsey, Y., Carter, N. P., Copeland, N., Gilbert, D. J., Jenkins, N. A., Agulnick, A., Forster, A. & Rabbitts, T. H. (1999) Mamm Genome 10, 1089-94.

Tsukamoto, K., Ito, N., Yoshimoto, M., Kasumi, F., Akiyama, F., Sakamoto, G., Nakamura, Y. & Emi, M. (1998) Cancer 82, 317-22.

Valge-Archer, V. E., Osada, H., Warren, A. J., Forster, A., Li, J., Baer, R., and Rabbitts, T. H. (1994) *Proc Natl Acad Sci USA* 91(18), 8617-21

Visvader, J. E., Elefanty, A. G., Strasser, A., and Adams, J. M. (1992) *Embo J* 11(12), 4557-64

Visvader, J. E., Mao, X., Fujiwara, Y., Hahm, K., and Orkin, S. H. (1997) *Proc Natl Acad Sci USA* 94(25), 13707-12

Visvader, J. E., Venter, D., Hahm, K., Santamaria, M., Sum, E. Y. M., O'Reilly, L., White, D., Williams, R., Armes, J., and Lindeman, G. J. (2001) *Proc Natl Acad Sci USA* 98(25), 14452-14457

Visvader, J., Begley, C. G. & Adams, J. M. (1991) Oncogene 6, 187-94.

Wadman, I. A., Osada, H., Grutz, G. G., Agulnick, A. D., Westphal, H., Forster, A., and Rabbitts, T. H. (1997) *Embo J* 16(11), 3145-57

Wadman, I., Li, J., Bash, R. O., Forster, A., Osada, H., Rabbitts, T. H., and Baer, R. (1994*Embo J* 13(20), 4831-9

Warren, A. J., Colledge, W. H., Carlton, M. B., Evans, M. J., Smith, A. J. & Rabbitts, T. H. (1994) Cell 78, 45-57.

Watters, D., Khanna, K. K., Beamish, H., Birrell, G., Spring, K., Kedar, P., Gatei, M., Stenzel, D., Hobson, K., Kozlov, S., Zhang, N., Farrell, A., Ramsay, J., Gatti, R., and Lavin, M. (1997) Oncogene 14(16), 1911-21

Weiss, M. J., Keller, G. & Orkin, S. H. (1994) Genes Dev 8, 1184-97.

Wilkinson, D. (1992) In Situ Hybridisation (IRL, New York).

Wilson, C. A., Ramos, L., Villasenor, M. R., Anders, K. H., Press, M. F., Clarke, K., Karlan, B., Chen, J. J., Scully, R., Livingston, D., Zuch, R. H., Kanter, M. H., Cohen, S., Calzone, F. J., and Slamon, D. J. (1999) *Nat Genet* 21(2), 236-40

Wong, A. K., Ormonde, P. A., Pero, R., Chen, Y., Lian, L., Salada, G., Berry, S., Lawrence, Q., Dayananth, P., Ha, P., Tavtigian, S. V., Teng, D. H., and Bartel, P. L. (1998) *Oncogene* 17(18), 2279-85

Yamada, Y., Warren, A. J., Dobson, C., Forster, A., Pannell, R., and Rabbirts, T. H. (1998) *Proc Natl Acad Sci USA* 95(7), 3890-5

Yu, X. (2000), PhD thesis

Yu, X., and Baer, R. (2000) *J Biol Chem* 275(24), 18541-9

Yu, X., Wu, L. C., Bowcock, A. M., Aronheim, A., and Baer, R. (1998) *J Biol Chem* 273(39), 25388-92

Zhang, H., Somasundaran, K., Peng, Y., Tian, H., Bi, D., Weber, B. L., and El-Deiry, W. S. (1998) *Oncogene* 16(13), 1713-21

---

The invention claimed is:

1. A method for detecting an aberrant mammary epithelial cell in a subject or in a biological sample from said subject, said method comprising contacting cells or cell extracts from said subject or said biological sample with an antibody specific for LIM domain only 4 (LMO4), screening for the level of antibody-LMO4 complex formation, comparing the level of the LMO4-antibody complex in the cells from said subject or said sample with the level of the LMO4-antibody complex in normal cells, and determining the presence of an aberrant mammary epithelial cell based on an elevated level of the LMO4-antibody complex in the cells from said subject or said sample relative to normal mammary epithelial cells.

2. A method for diagnosing the presence of breast cancer in a subject, said method comprising contacting cells or cell extracts from said subject or a biological sample from said subject with a LMO4-binding effective amount of an antibody having specificity for said LMO4, quantitatively or qualitatively determining the level of a LMO4-antibody complex, comparing the level of the LMO4-antibody complex in the cells from said subject or said sample with the level of the LMO4-antibody complex in normal cells, and determining the presence of breast cancer based on an elevated level of the LMO4-antibody complex in the cells from said subject or said sample relative to normal cells.

3. The method according to claim 1 wherein said antibody is selected from:
   (i) a deimmunized antibody molecule having specificity for an epitope recognized by a monoclonal antibody specific for LMO4 wherein said antibody is deimmunized with respect to the host into which it will be introduced;
   (ii) an isolated monoclonal antibody wherein said antibody interacts with LMO4;
   (iii) the monoclonal antibody secreted by hybridoma 16H2 (ECACC Accession No. 03052001);
   (iv) the monoclonal antibody secreted by hybridoma 20F8 (ECACC Accession No. 03052002).

4. A method of detecting, LMO4 in a sample, comprising contacting the sample with an antibody or a fragment thereof specific for LMO4, detecting the level of a complex comprising said antibody or said fragment and LMO4, and comparing the level of said complex in said sample with the level of complex in normal controls and determining an indication of breast cancer growth based on an elevated level of the complex in said sample relative to said normal controls.

5. The method according to claim 4 wherein said antibody is selected from:
   (i) a deimmunized antibody molecule having specificity for an epitope recognized by a mono clonal antibody specific for LMO4 wherein said antibody is deimmunized with respect to the host into which said antibody will be introduced;
   (ii) an isolated monoclonal antibody wherein said antibody interacts with LMO4;
   (iii) the monoclonal antibody secreted by hybridoma 16H2 (ECACC Accession No. 03052001);
   (iv) the monoclonal antibody secreted by hybridoma 20F8 (ECACC Accession No. 03052002).

6. A method for detecting an aberrant mammary epithelial cell in a subject or in a biological sample from said subject, said method comprising contacting cells or cell extracts from said subject or said biological sample with an antibody or fragment thereof specific for LMO4, and detecting an elevated level of LMO4 relative to a normal cell as indicative of an aberrant mammary epithelial cell.

\* \* \* \* \*